(12) United States Patent
Fekete et al.

(10) Patent No.: US 8,828,664 B2
(45) Date of Patent: **\*Sep. 9, 2014**

(54) SAMPLE PREPARATION FOR IN SITU NUCLEIC ACID ANALYSIS, METHODS AND COMPOSITIONS THEREFOR

(71) Applicant: Applied Biosystems, LLC, Carlsbad, CA (US)

(72) Inventors: Richard Fekete, Austin, TX (US); Annalee Nguyen, Austin, TX (US)

(73) Assignee: Applied Biosystems, LLC., Carlsbad, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 14/136,685

(22) Filed: Dec. 20, 2013

(65) Prior Publication Data

US 2014/0127692 A1    May 8, 2014

Related U.S. Application Data

(60) Division of application No. 13/650,853, filed on Oct. 12, 2012, which is a continuation of application No. 13/157,840, filed on Jun. 10, 2011, now Pat. No. 8,288,106, which is a division of application No. 12/122,274, filed on May 16, 2008, now Pat. No. 7,964,350, said application No. 13/157,840 is a division of application No. 12/122,274, filed on May 16, 2008, now Pat. No. 7,964,350.

(60) Provisional application No. 60/938,978, filed on May 18, 2007.

(51) Int. Cl.
*C12Q 1/68* (2006.01)
*C12P 19/34* (2006.01)

(52) U.S. Cl.
CPC .................................. *C12Q 1/686* (2013.01)
USPC ......... 435/6.12; 435/91.1; 435/91.2; 536/25.4

(58) Field of Classification Search
USPC .................. 435/6.12, 91.1, 91.2; 536/25.4
See application file for complete search history.

(56) References Cited

U.S. PATENT DOCUMENTS

| | | |
|---|---|---|
| 4,596,789 A | 6/1986 | Dutta et al. |
| 4,691,007 A | 9/1987 | Dutta et al. |
| 4,910,190 A | 3/1990 | Bergespm et al. |
| 4,997,932 A | 3/1991 | Reardon et al. |
| 5,008,245 A | 4/1991 | Digenis |

(Continued)

FOREIGN PATENT DOCUMENTS

| | | |
|---|---|---|
| EP | 0261956 | 3/1988 |
| EP | 0410411 | 1/1991 |

(Continued)

OTHER PUBLICATIONS

Barbacci, E. et al., "Variant Hepatocyte Nuclear Factor 1 is required for visceral endoderm specification", *Development*, 126, 1999, pp. 4795-4805.

(Continued)

*Primary Examiner* — Kenneth Horlick

(57) ABSTRACT

Sample preparation processes for in situ RNA or DNA analysis, methods and compositions therefor are provided. Processes provided herein allow DNA or RNA analysis to be carried out in the same tube or on an aliquot of the prepared sample without centrifugation or extraction. The preparation process can be carried out at room temperature in as little as seven minutes and is amenable to high throughput processing using manual or robotic platforms.

28 Claims, 15 Drawing Sheets

(56) References Cited

U.S. PATENT DOCUMENTS

Figure 1A:
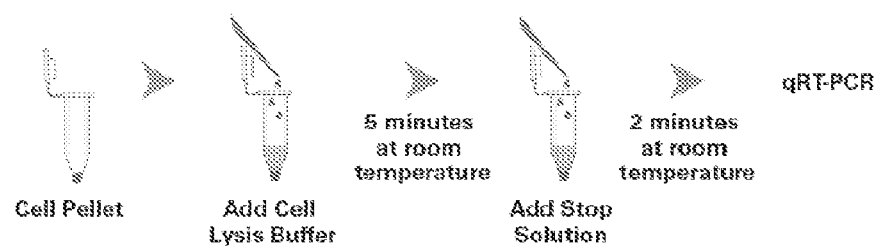

| | | | |
|---|---|---|---|
| 5,055,450 | A | 10/1991 | Edwards et al. |
| 5,194,588 | A | 3/1993 | Edwards et al. |
| 5,284,829 | A | 2/1994 | McKerrow et al. |
| 5,364,763 | A | 11/1994 | Kacian |
| 5,386,024 | A | 1/1995 | Kacian et al. |
| 5,414,132 | A | 5/1995 | Stein et al. |
| 5,554,516 | A | 9/1996 | Kacian et al. |
| 5,693,467 | A | 12/1997 | Roblin, III et al. |
| 5,726,021 | A | 3/1998 | Britschgi et al. |
| 5,726,158 | A | 3/1998 | Edwards et al. |
| 5,871,628 | A | 2/1999 | Dabiri et al. |
| 5,871,975 | A | 2/1999 | Kacian et al. |
| 5,891,636 | A | 4/1999 | Van Gelder et al. |
| 5,907,068 | A | 5/1999 | Stein et al. |
| 5,939,262 | A | 8/1999 | Pasloske et al. |
| 6,111,096 | A | 8/2000 | Laugharn et al. |
| 6,204,375 | B1 | 3/2001 | Lader |
| 6,218,105 | B1 | 4/2001 | Hall et al. |
| 6,218,531 | B1 | 4/2001 | Ekenberg |
| 6,265,165 | B1 | 7/2001 | Xu et al. |
| 6,313,285 | B1 | 11/2001 | Butler et al. |
| 6,329,179 | B1 | 12/2001 | Kopreski |
| 6,528,641 | B2 | 3/2003 | Lader |
| 6,583,301 | B1 | 6/2003 | Eaton et al. |
| 6,610,475 | B1 | 8/2003 | Kacian et al. |
| 6,664,379 | B1 | 12/2003 | Kudlicki et al. |
| 6,740,647 | B1 | 5/2004 | Baucke et al. |
| 6,825,340 | B2 | 11/2004 | Pasloske et al. |
| 7,001,724 | B1 | 2/2006 | Greenfield |
| 7,067,298 | B2 | 6/2006 | Latham et al. |
| 7,163,793 | B2 | 1/2007 | Kudlicki et al. |
| 7,214,484 | B2 | 5/2007 | Weber et al. |
| 7,964,350 | B1 | 6/2011 | Fekete et al. |
| 8,211,637 | B2 | 7/2012 | Kore et al. |
| 8,288,106 | B2 | 10/2012 | Fekete et al. |
| 2001/0049133 | A1 | 12/2001 | McCabe et al. |
| 2002/0026046 | A1 | 2/2002 | Pasloske et al. |
| 2002/0172972 | A1 | 11/2002 | Tabor et al. |
| 2002/0177139 | A1 | 11/2002 | Greenfield et al. |
| 2003/0170617 | A1 | 9/2003 | Pasloske |
| 2004/0038213 | A1 | 2/2004 | Kwon |
| 2004/0115658 | A1 | 6/2004 | Weber et al. |
| 2005/0009045 | A1 | 1/2005 | Greenfield et al. |
| 2005/0014169 | A1 | 1/2005 | Latham et al. |
| 2005/0069953 | A1 | 3/2005 | Fang et al. |
| 2005/0158783 | A1 | 7/2005 | Simms |
| 2005/0277121 | A1 | 12/2005 | Pasloske et al. |
| 2006/0068480 | A1 | 3/2006 | Christophers et al. |
| 2006/0115844 | A1 | 6/2006 | Finkelstein et al. |
| 2006/0148006 | A1 | 7/2006 | Fang et al. |
| 2006/0188892 | A1 | 8/2006 | Latham et al. |
| 2006/0269536 | A1 | 11/2006 | Deperthes et al. |
| 2007/0032418 | A1 | 2/2007 | Shapiro et al. |
| 2010/0159482 | A1 | 6/2010 | Kore et al. |
| 2013/0004941 | A1 | 1/2013 | Kore et al. |

FOREIGN PATENT DOCUMENTS

| | | |
|---|---|---|
| EP | 1044984 | 10/2000 |
| EP | 1476573 | 1/2010 |
| EP | 2367954 | 9/2011 |
| WO | WO-93/15228 | 8/1993 |
| WO | WO-94/26867 | 11/1994 |
| WO | WO-96/00228 | 1/1996 |
| WO | WO-00/17320 | 3/2000 |
| WO | WO-01/21830 | 3/2001 |
| WO | WO-01/42507 | 6/2001 |
| WO | WO-03/002716 | 1/2003 |
| WO | WO-03/064605 | 7/2003 |
| WO | WO-2010/071833 | 6/2010 |

OTHER PUBLICATIONS

EP03710760.4 EPO Communication pursuant to Article 96(2) EPC mailed Apr. 5, 2006.

EP03710760.4 EPO Communication pursuant to Article 96(2) EPC mailed Mar. 2, 2007.

EP03710760.4 EPO Invitation pursuant to Article 94(3) and Rule 71(1) EPC mailed Mar. 12, 2008.

EP03710760.4 EPO Communication under Rule 71(3) EPC mailed Aug. 18, 2009.

EP03710760.4 EPO Communication Decision to grant a European patent pursuant to Article 971(1) EPC mailed Dec. 10, 2009.

EP03710760.4 EPO Communication of a Notice of Opposition by bioMerieux mailed Oct. 13, 2010.

EP03710760.4 Summons to Attend Oral Proceedings with Preliminary non-binding opinion of the Opposition Division mailed Jul. 27, 2011.

EP03710760.4, EPO Brief Communication mailed Dec. 6, 2011.

EP03710760.4 Life Technologies Corporation's Comments Faxed Dec. 29, 2011.

EP03710760.4 EPO Communication of Notice of Opposition filed by Konig Szynka Tilmann von Renesse mailed Oct. 19.

EP03710760.4 Response to Late Submission of Opponent 1 in Preparation for Oral Proceedings Faxed on Jan. 16, 2012.

EP03710760.4 Konig Szynka Tilmann von Renesse Response to Life Technologies Response dated Dec. 29, 2011 Faxed on Jan. 9, 2012.

EP03710760.4 Decision on Oral Proceedings mailed Mar. 5, 2012.

EP03710760.4 Minutes of Oral Proceedings mailed Mar. 5, 2012.

EP03710760.4 Communication to the parties concerning termination of opposition proceedings mailed Jun. 21, 2012.

EP03710760.4 Termination of Opposition Proceedings of Patent No. 03710760.4 with Revocation of Patent mailed Jun. 14, 2012.

EP09180993.9, Communication pursuant to Article 94(3) in European Patent Application 09180993.9 mailed Jan. 25, 2011 5 pages.

EP09180993.9 "Examination Report".

EP09180993.9 Response to Office Action Mailed Jan. 25, 2011, Filed Jul. 8, 2011, 3 pages.

EP10182642.8 Communication pursuant to Article 94(3) mailed Oct. 26, 2011.

EP10182642.8 Extended European Search Report mailed Jan. 26, 2011, 7 pages.

Xu, R. et al., "One-Step Analysis and Quantification of RNA by RT-PCR: Using High-Temperature Reverse Transcription", *Focus*, vol. 22(1), 2000, pp. 3-5.

Ambion, , "Online Catalog Dec. 12, 2010-Jan. 19, 2011", *Cells-to-cDNA II,Reverse Transcription Kit*, 2 pages.

Ambion, , "Press Release", web.archive.org/web/200206031230/ http://ambion.com/news.

Applied Biosystems, , "TaqMan MicroRNA Cells to CT Kit", Product Bulletin, Nov. 2007.

Applied Biosystems, , "Testing of beta-formulation of Cells-to-cDNA III", Powerpoint presentation to Glaxo Smith Kline, Aug. 3, 2006.

Baum, L. et al., "Regulation of expression of cytochrome P-450 2D mRNA in rat brain with steroid hormones", *Brain Research*, vol. 765, 1997, pp. 67-73.

Betzel, C. et al., "Active-site geometry of proteinase K", *FEBS Letters, Elsevier*, Amsterdam, NL, vol. 197, No. 1-2,, Mar. 3, 1986, 105-110.

Brady, G. et al., "Construction of cDNA Libraries from Single Cells", *Methods Enzymol.*, 225, 1993, pp. 611-623.

Busche, S et al., "Expression of Angiotensin AT1 and AT2 Receptors in Adult Rat Cardiomyocytes after Myocardial Infarction: A Single-Cell Reverse Transcriptase-Polymerase Chain Reaction Study", *Am. J. Pathol.*, 157, 2000, pp. 605-611.

Dhamne, C. et al., "The chloromethylketone protease inhibitor AAPF(CMK) also targets ATP-dependent helicases and SAP-domain proteins", *Journal of Cellular Biochemistry*, vol. 100, No. 3,, Feb. 2, 2007, 716-726.

Edmands, S. et al., "Rapid RT-PCR amplification from limited cell numbers", *Genome Research 3*, 1994, pp. 317-319.

Elbashir, S. et al., "Analysis of Gene Function in Somatic Mammalian Cells Usinq Small interfering RNAs", *Methods*, vol. 26 (2), Feb. 1, 2002, 199-213.

EP03710760.4 "European Search Report mailed Nov. 3, 2005".

EP09180993.9 "EP Search Report", Feb. 11, 2010.

EP09796899.4 "Examination Report", Mailed Oct. 29, 2012.

(56) References Cited

OTHER PUBLICATIONS

EP10182642.8 "Extended European Search Report Mailed Jan. 26, 2011", 7.

Fekete, et al., "Applied Biosystems Streamlined, High-throughput Assessment of siRNA-mediated Gene Knockdown in 384-23II Plates by Performing qRT-PCT from Cell Lysates", Abstract, presentation at Merck, Mar. 7, 2007.

Fink, L. et al., "Immunostaining and laser-assisted cell picking for mRNA analysis", Laboratory Invest., 80, 2000, pp. 327-333.

Fink, L. et al., "Immunostaining for cell picking and real-time mRNA quantitation", Am. J. Pathol., vol. 157(5), Nov. 2000, pp. 1459-1466.

Fink, L. et al., "Rat Porphobilinogen Deaminase Gene: A Pseudogene-Free Internal Standard for Laser-Assisted Cell Picking", BioTechniques, 26, 1999, 510-516.

Fung, M. et al., "PCR amplification of mRNA directly from a crude cell lystate prepared by thermophilic protease digestion", Nucl. Acids Res., vol. 19(15), 1991, pp. 4300.

Genechoice, , "cDNA Direct from Cells RT Kit", from pgcsci.com/genechoice/GeneChoice_18.html, downloaded Jan. 28, 2002.

Goldenberger, D. et al., "A simple "universal" DNA extraction procedure using SDS and proteinase K is compatible with direct PCR amplification", PCR Methods and Applications 4, 1995, pp. 368-370.

Hayashi, Y. et al., "A simple single-tube procedure of PCR assay for the detection of hepatitis C virus RNA", Research in Virology 145, 1994, pp. 123-128.

Invitrogen, "CellsDirect One-Step qRT-PCR Kits User Manual, Aug. 16, 2006".

Invitrogen, , "SuperScript III Platinum CellsDirect two-Step 1RT-PCR Kit Instruction Manual, Nov. 12, 2004".

Ivarsson, K. et al., "Evaluation of the Effects of DNase Treatment on Signal Specificity in RT-PCR and In Situ RT-PCR", BioTechniques, 25, 1998, pp. 630-638.

Jena, P. et al., "Amplification of genes, single transcripts and cDNA libraries from one cell and direct sequence analysis of amplified products derived from one molecule", Journal of Immunological Methods, vol. 190, 1996, pp. 199-213.

Jiang, Y, et al., "A Rapid RT-PCR Method for Detection of Intact RNA in Formalin-Fixed Paraffin-Embedded Tissues", Nuc. Acids Research, vol. 23(15), Jan. 1, 1995, pp. 3071-3072.

Kher, R. et al., "Direct in situ reverse transcriptase-polymerase chain reaction", Am. J. Physiol. Cell Physiol., 281, 2001, pp. C726-C732.

Klebe, R. et al., "RT-PCR Without RNA Isolation", BioTechniques, 21, 1996, pp. 1094-1100.

Kobs, G. , "Isolation of RNA from Plant, Yeast and Bacteria", Promega Notes No. 68, 1998, p. 29.

Kore, A. R. et al., "Synthesis and application of MeOSuc-Ala-Ala-Pro-Phe-CH2Cl as potent proteinase K inhibitor", Bioorganic & Medicinal Chemistry Letters, Pergamon, Elsevier Science, vol. 19 (5), Mar. 1, 2009, 1296-1300.

Kudla, et al., "RNA editing in tobacco chloroplasts leads to the formation of the translatable psbL mRNA by a C to U substitution within the initiation codon", EMBO J., 11(3), 1992, pp. 1099-1103.

Lysis, , "downloaded Feb. 28, 2011", http://en.wikipedia.org/wiki/Lysis.

Martinez, et al., "Non-radioactive localization of nucleic acids by direct in situ PCR and in situ RT-PCR in paraffin-embedded sections", J. Histochem. Cytochem., 43:8, 1995, pp. 739-747.

Mensink, E. et al., "Quantitation of minimal residual disease in Philadelphia chromosome positive chronic myeloid leukaemia patients using real-time quantitative rT-PCR", Br. J. Haematol., 102, 1998, pp. 768-774.

Navia, M. et al., "Structure of human neutrophil elastase in complex with a peptide chloromethyl ketone inhibitor 1.84-Å resolution", Proc. Natl. Acad. Sci. USA, vol. 86, 1989, 7-11.

New England Biolabs, , "Catalog, 1993-1994", 1993-1994, 96.

O'Brien, D. et al., "RT-PCR assay for detection of transcripts from very few cells using whole cell lysates", BioTecjniques, vol. 16(4), 1994, 587, 588, 590.

O'Leary, , "Reducing the Impact of Endogenous Ribonucleases on Reverse Transcription-PCR Assay Systems", Clin. Chem., vol. 45(4), 1999, pp. 449-450.

PCT/US09/68819 "International Preliminary Report on Patentability mailed Jun. 30, 2011", 9 pgs.

PCT/US09/68819 International Search Report & Written Opinion mailed Mar. 30, 2010.

PCT/US2003/02439 International Preliminary Examination Report Issued Jun. 11, 2004.

PCT/US2003/02439 International Search Report Mailed Dec. 10, 2003, 2 pages.

Peet, N. et al., "Synthesis of Peptidyl Fluoromethyl Ketones and Peptidyl Alpha-Keto Esters as Inhibitors of Porcine Pancreatic Elastase , Human Neutrophil Elastase, and Rat and Human Neutrophil Cathespin G", J. Medicinal Chem., vol. 33(1), Jan. 1, 1990, pp. 394-407.

Pereira, P. J. et al., "The 2.2 A crystal structure of human chymase in complex with succinyl-ala-ala-pro-phe-chloromethylketone: structural explanation for its dipeptidyl carboxypeptidase specificity", Journal of Molecular Biology, London, GB, vol. 286, No. 1,, Feb. 12, 1999, 163-173.

Phillips, J. et al., "Antisense RNA Amplification: A Linear Amplification Method for Analyzing the mRNA Population from Single Living Cells", Methods, 10, 1996, pp. 283-288.

Powers, J. et al., "Reaction of Serine Proteases with Halomethyl Ketones", Methods in Enzymology, vol. 46, 1977, 197-208.

Powers, J. et al., "Specificity of Porcine Pancreatic Elastase, Human Leukocyte Elastase and Cathepsin G", Biochimicia et Biosysica Acts, vol. 485, 1977, 156-166.

Price, et al., "Properties of Chromatographically Purified Bovine Pancreatic Deoxyribonuclease", J. Biol. Chem., 244(4), 1969, 917-923.

Promega, , "RQ1 RNase-Free DNase", Promega Technical Bulletin No. 518, Feb. 2000, pp. 1-4.

Qiagen, , FastLane Kits—from Sample Direct to Resutl, Jan. 2007.

Qiagen, , "RNeasy Mini Handbrook: RNeasy Mini Protocol for Isolation of Total RNA from Animal Tissues", Jun. 2001.

Reilly, C. F. et al., "The degradation of human lung elastin by neutrophil proteinases", Biochimica et Biophysica Acta, vol. 621, 1980, 147-157.

Roche Applied Science, , "ProteinaseK, Catalog No. P6556", 2003.

Sellner, L. N. et al., "Reverse transcripts inhibits Taq polymerase activity", Nucleic Acids Research, vol. 20, No. 7, 1992, 1487-1490.

Shi, et al., "Direct reverse transcription-polymerase chain reaction from whole blood without RNA extraction", Genetic Analysis: Biomolecular Engineering, 9:5-6, 1992, pp. 149-150.

Sigma-Aldrich, , "Product Information: Proteinase K, Catalog No. P6556", 2003.

Simon, S. et al., "Detection of Phosphatidylinositol Glycan Class A Gene Transcripts by RT In Situ PCR Hybridization: A Comparative Study Using Fluorescein, Texas Red, and Digoxigenn-11 dUTP for Color Detection", J. Histochem. Cytochem., vol. 45(12), 1997, pp. 1659-1664.

Specht, K. et al., "Quantitative Gene Expression Analysis in Microdissected Archival Formalin-Fixed and Paraffin-Embedded Tumor Tissue", American Jorunal of Pathology, vol. 158, vol. 158, 2001, pp. 419-429.

Stahlberg, et al., "Properties of the Reverse Transcription Reaction in mRNA Quantification", Clin Chem, 50(3), 2004, 509-515.

Stein, et al., "Mechanism of Inactivation of Human Leukocyte Elastase by a Chloromethyl Ketone: Kinetic and Solvent Isotope Effect Studies", Biochem., 25, 1986, 5414-5419.

Stein, R. , "Catalysis by Human Leukocyte Elastase: Substrate Structural Dependence of Rate-Limiting Protolytic Catalysis and Operation of the Charge Relay System", J. Am. Chem. Soc., 105, 1983, 5111-5116.

(56) References Cited

OTHER PUBLICATIONS

Stratagene, , "SideStep QPCRcDNA Synthesis Kit Instruction Manual", 2007.
Su, et al., "High-throughput RT-PCT analysis of multiple transcripts using a microplate RNA isolation procedure", *BioTechniques*, 22, 1997, pp. 1107-1113.
Sumida, A. et al., "Evaluation of Induction of CYP3A mRNA Using the HepG2 Cell Line and Reverse transcription-PCR", *Biol. Pharm. Bull.*, vol. 22(1), 1999, pp. 61-65.
Tang, J. et al., "A polymerase chain reaction based method for detecting Mycoplasma/Acholeplasma contaminants in cell culture", *J. Microbiological Methods*, 39, 2003, pp. 121-126.
Tel-Test, Inc., , "RNA Stat-60", isotexdiagnostics.com/rna_stat-60_reagent.tml, cited in Baum et al, 1997.
Tullis, R. et al., "Calcium Protects DNase I from Proteinase K: A New Method for the Removal of Contaminaing RNase from DNase I", *Analytical Biochemistry*, 107, 1980, pp. 260-264.
Webster's, , "Third New International Dictionary, 1993, p. 1448".
Webster's, , "Third New International Dictionary, 1993, p. 28".
Webster's, , "Third New International Dictionary,1993, p. 641".
Wolf, W. et al., "Inhibition of Proteinase K by Methoxysuccinyl-Ala-Ala-Pro-Ala-Chloromethyl Ketone An X-ray Study at 2.2-A Resolution", *Journal of Biological Chemistry*, vol. 266 (26), 1991, pp. 17695-17699.
Yan, L. et al., "One-tube protocol for single-cell reverse transcriptase-polymerase chain reaction", *Anal. Biochem*, 304, 2002, pp. 267-270.

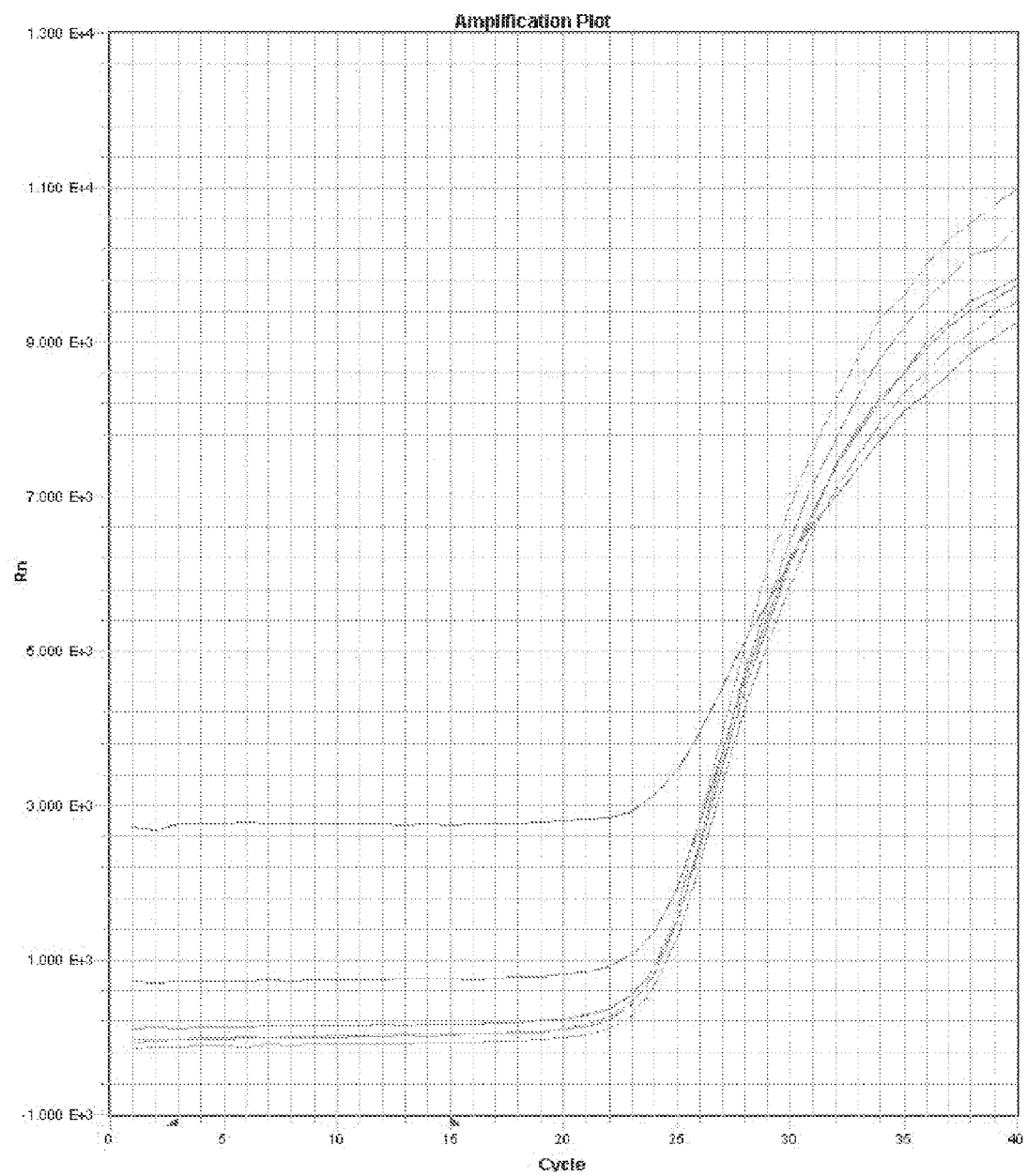

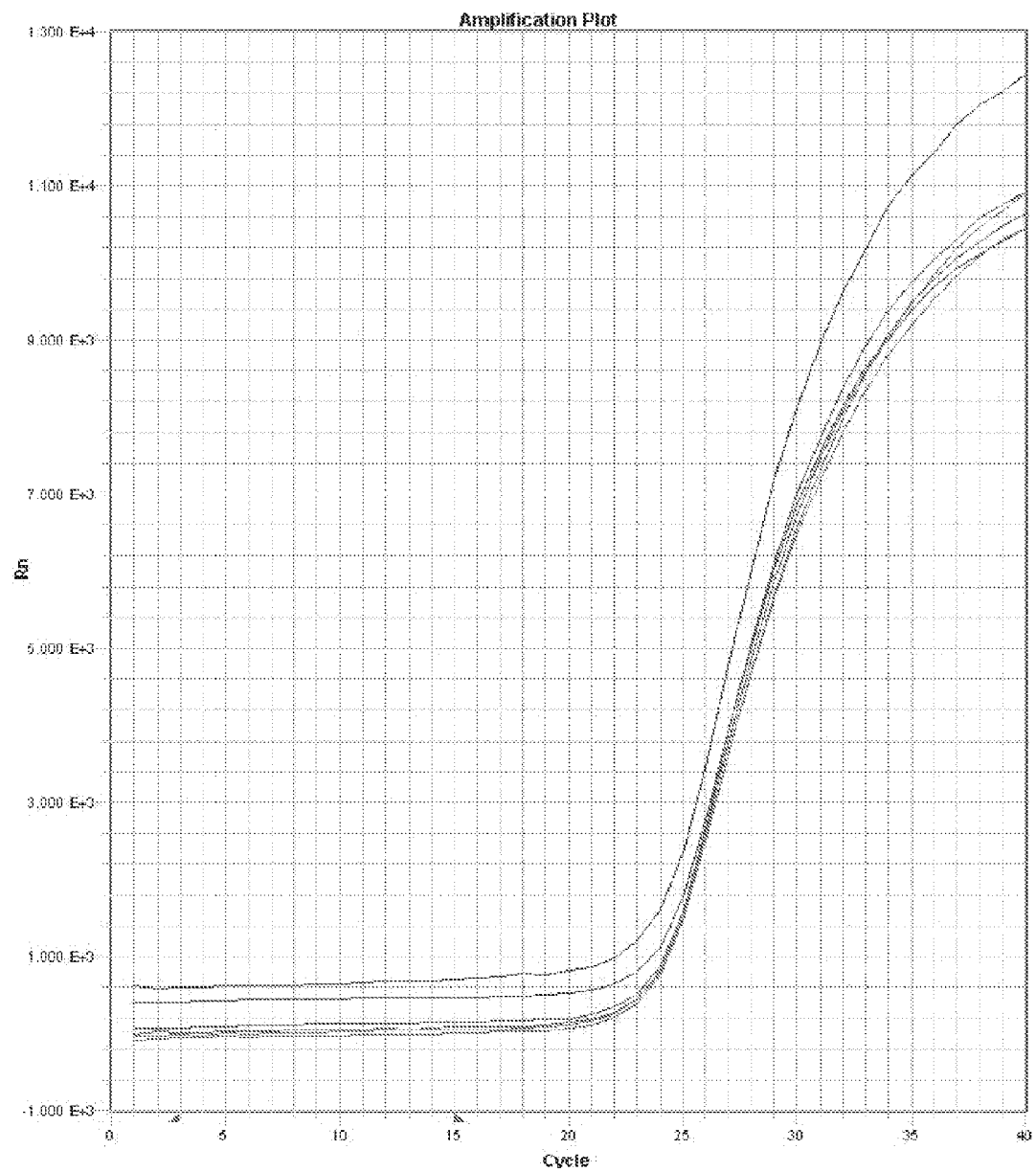

SAMPLE PREPARATION FOR IN SITU NUCLEIC ACID ANALYSIS, METHODS AND COMPOSITIONS THEREFOR

The present application is a divisional application of currently pending U.S. application Ser. No. 13/650,853 filed Oct. 12, 2012, which is a continuation application of U.S. application Ser. No. 13/157,840 filed Jun. 10, 2011, now U.S. Pat. No. 8,288,106, Oct. 16, 2012, which application is a divisional application of U.S. application Ser. No. 12/122,274 filed May 16, 2008, now U.S. Pat. No. 7,964,350, Jun. 21, 2011, which application claims the benefit of U.S. Provisional Application No. 60/938,978 filed May 18, 2007. The contents of all applications are incorporated herein in their entirety.

The U.S. government has certain rights in this application pursuant to Grant No. R44HL69718 from the National Institutes of Health.

FIELD

The present teachings generally relate to compositions, processes, methods, and kits for preparation of samples containing genetic material for analysis, detection and/or quantitation.

INTRODUCTION

Real-time polymerase chain reaction (PCR) is routinely used for detection of nucleic acid, and real-time quantitative reverse transcriptase-PCR (qRT-PCR) is routinely used for detection of RNA and for studying gene expression. However, current procedures for carrying out RT-PCR directly on cell lysates are not amendable to high throughput analysis using robotic workstations. For example, procedures for preparation of nucleic acid for detection requiring temperature shifts make controlling temperature across an entire plate or block a challenge. Certain current procedures also contain components that are inhibitory for optimum reverse transcriptase function or for optimum DNA polymerase function. The present teachings provide composition, method and kit embodiments for preparation of samples for detection and/or quantitation of nucleic acid that are amenable to high throughput analyses.

SUMMARY

Certain trademarked products are cited by teachings herein with reference to surfactants. Generic descriptions for such products are as follows: TRITON X-100™, octylphenol ethoxylate having an average of 9.5 ethoxylate groups (Dow Chemical Company Product Information, Form No. 119-01882, JMS1206); TRITON X-114™, octylphenol ethoxylate having an average of 7.5 ethoxylate groups (Dow Chemical Company Product Information, Form No. 119-01884, JMS 1206); NONIDET P-40™, octylphenolpoly(ethyleneglycolether) (Roche Diagnostics GmbH, Catalog No. 11 332 473 001, July 2005); and THESIT™, dodecyl alcohol polyoxyethylene ether (IUPAC Name 2-dodecoxyethanol; CAS Number 9002-92-0; Chemical Formula $C_{14}H_{30}O_2$).

Sample preparation process embodiments provided by teachings herein include a process for preparing a sample containing RNA for in situ analysis of RNA or a surrogate thereof. In some embodiments, the process comprises contacting the sample containing RNA with a lysis mixture under conditions and for a time to produce a lysate, and admixing the lysate with a stop mixture at substantially the same temperature as the contacting step to form a stopped mixture. For such embodiments, the lysis mixture comprises a polypeptide having protease activity, a polypeptide having deoxyribonuclease activity, and a surfactant that substantially lacks fluorescence between 300 nm and 750 nm when in use for in situ analysis of RNA or a surrogate thereof. Also, for such embodiments, the lysis mixture is substantially free of a cation chelator. The stop mixture comprises a cation chelator effective to inactivate the polypeptide having deoxyribonuclease activity, and an inhibitor of the polypeptide having protease activity. The resultant stopped mixture is compatible with in situ reverse transcriptase and DNA polymerase reactions. In some embodiments, the stop mixture further comprises a peptide or molecule having ribonuclease inhibitory activity.

In certain embodiments, the stopped mixture can be further combined with reagents for reverse transcription to form a first amplification mixture and, in some embodiments, the first amplification mixture is placed in contact with reagents for quantitative polymerase chain reaction (qPCR) amplification. In some embodiments, reagents for qPCR amplification comprise a green, yellow or orange emitter, and the process further comprises carrying out in situ analysis of the DNA, RNA, or a surrogate thereof comprising detecting fluorescence of the green, yellow, or orange emitter, respectively.

For certain embodiments, the sample preparation process of contacting and admixing are carried out at substantially the same temperature, which temperature is from 15° C. to 30° C., 16° C. to 28° C. or 19° C. to 25° C. as further described infra.

In some embodiments, a process for preparing a sample containing RNA for in situ analysis of RNA or a surrogate thereof is provided, which process comprises contacting the sample containing RNA with a lysis mixture at 16° C. to 28° C. for a time to produce a lysate, and admixing the lysate with a stop mixture at substantially the same temperature as the contacting step to form a stopped mixture. For such embodiments, the lysis mixture comprises proteinase K or an enzymatically active mutant or variant thereof, DNase I, and a surfactant comprising TRITON X-114™ at a concentration from 0.02% to 3%, or 0.05% to 2%, or 0.05% to 1%, THESIT™ at a concentration of 0.01% to 5%, or 0.02% to 3%, or 0.05% to 2%, or 0.05% to 1%, or 0.05% to 0.5%, or 0.05% to 0.3%, TRITON X-100™ at a concentration of 0.05% to 3%, or 0.05% to 1%, or 0.05% to 0.3%, NONIDET P-40™ at a concentration of 0.05% to 5%, or 0.1% to 3%, or 0.1% to 2%, or 0.1% to 1% or 0.1% to 0.3% or 0.1% to 5%, or a combination thereof, and wherein the lysis mixture is substantially free of a cation chelator. Also for such embodiments, the stop mixture comprises a cation chelator in an amount effective to inactivate DNase I, and a methoxysuccinyl-Ala-Ala-Pro-Val-haloalkyl ketone (AAPV, SEQ ID NO:1) wherein the halo is chloro, bromo, iodo, or fluoro and the alkyl is $C_1$-$C_3$, such as methoxysuccinyl-Ala-Ala-Pro-Val-chloromethyl ketone (AAPV, SEQ ID NO:1) or an active mutant or analog thereof. In some embodiments, the lysis mixture further comprises a calcium salt, a reducing agent, or a combination thereof. In some embodiments, the calcium chelator of the stop mixture comprises ethylene glycol tetraacetic acid (EGTA). In further embodiments, the stop mixture comprises a ribonuclease inhibitor.

Sample preparation processes for samples containing DNA for in situ analysis of DNA or a surrogate thereof are provided by other embodiments herein. Such process embodiments comprise contacting the sample containing DNA with a lysis mixture at 16° C. to 28° C. for a time and under conditions to produce a lysate, and admixing the lysate with a stop mixture at substantially the same temperature as the contacting step. For such embodiments, the lysis mixture comprises a polypeptide having protease activity, and a surfactant comprising TRITON X-114™ at a concentration from 0.02% to 3%, or 0.05% to 2%, or 0.05% to 1%, THESIT™ at a concentration of 0.01% to 5%, or 0.02% to 3%, or 0.05% to 2%, or 0.05% to 1%, or 0.05% to 0.5%, or 0.05% to 0.3%, TRITON X-100™ at a concentration of 0.05% to 3%, or 0.05% to 1%, or 0.05% to 0.3%, NONIDET P-40™ at a concentration in the lysis mixture of 0.05% to 5%, or 0.1% to 3%, or 0.1% to 2%, or 0.1% to 1% or 0.1% to 0.3%, or 0.1% -5%, or a combination thereof. In further embodiments, the lysis mixture comprises a peptide with ribonuclease activity. In addition, embodiments of the stop mixture comprise an inhibitor of the polypeptide having protease activity. Such an inhibitor has little to no inhibitory activity on DNA polymerase activity.

In further embodiments of teachings herein, a composition for cell lysis comprises proteinase K, DNase I, and a surfactant comprising TRITON X-114™ at a concentration of 0.05% to 1%, THESIT™ at a concentration of 0.05% to 0.3%, TRITON X-100™ at a concentration of 0.05% to 0.3%, NONIDET P-40™ at a concentration of 0.1% to 0.3%, or a combination thereof, wherein the composition is substantially free of a cation chelator. Embodiments of the composition for cell lysis can further comprise a calcium salt.

In some embodiments provided herein, a stop mixture is provided as a composition of matter, which composition comprises a cation chelator, a methoxysuccinyl-AAPV-haloalkyl ketone (SEQ ID NO:1) wherein the halo is chloro, bromo, iodo, or fluoro and the alkyl is $C_1$-$C_3$, and an inhibitor of a ribonuclease.

For certain embodiments, kits for preparation of a sample containing RNA for in situ detection of RNA or a surrogate thereof are provided wherein the kits comprise lysis solution components comprising a polypeptide having protease activity, and a surfactant comprising TRITON X-114™, THESIT™, TRITON X-100™, NONIDET P-40™, or a combination thereof, a polypeptide having deoxyribonuclease activity, wherein the lysis solution components are substantially free of a cation chelator; and stop mixture components comprising a cation chelator, an inhibitor of the polypeptide having protease activity, and, optionally, a ribonuclease inhibitor and a reducing agent.

Kit embodiments can further comprise one or more reagents for reverse transcription, such as reverse transcriptase, a reverse primer, dNTPs or a reverse transcriptase buffer, or can further comprise one or more reagents for PCR, such as a DNA polymerase, for example.

In some embodiments, processes and compositions are compatible with downstream nucleic acid detection methods using methods such as reverse transcription, polymerase chain reaction, qPCR, qRT-PCR, melt curve analysis, sequencing, message amplification, preamplification, detection, linear amplification for array analysis, and others that use CYANINE™ 3 or CYANINE™ 5 in array analysis, for example. As an example of compatibility, results for detection of miR-21 using sample preparation embodiments described herein were similar to results from using the MIRVANA™ kit for isolation of miRNA.

Sample preparation processes provided by embodiments herein are useful for any method where RNA or DNA is analyzed, e.g., detected or quantitated. Stopped samples may be used for genotyping analysis, gene expression analysis, copy number analysis, DNA methylation analysis, SNP genotyping, plant cell genotyping, or RNA analysis including, for example, analysis, detection or quantitation of mRNA and noncoding RNA such as, for example, rRNA, siRNA, snRNA, or miRNA.

Sample preparation embodiments presented by teachings herein provide surprisingly fast, efficient, and ambient temperature production of a lysate that is RT and PCR ready due, in part, to provision of conditions under which a protease and a deoxyribonuclease can carry out enzymatic activity at the same time and in the same reaction mixture. Sample preparation embodiments presented herein can be performed on cells that are in suspension or on cells that are attached to a growth surface such as for 96- or 384-well culture plates. These and other features of the present teachings will become more apparent from the description herein.

DRAWINGS

The skilled artisan will understand that the drawings, described below, are for illustration purposes only. The drawings are not intended to limit the scope of the present teachings in any way.

FIG. 1A provides a schematic diagram depicting a general overview of certain exemplary embodiments of the teachings herein for preparation of nucleic acid for analysis.

Figure 1B:
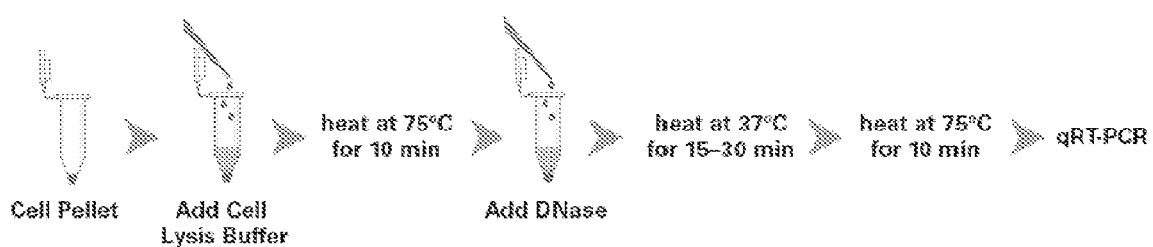

FIG. 1B provides a schematic diagram depicting a general overview of typical existing cell lysate based sample preparation methods involving multiple temperature steps.

Figure 2:
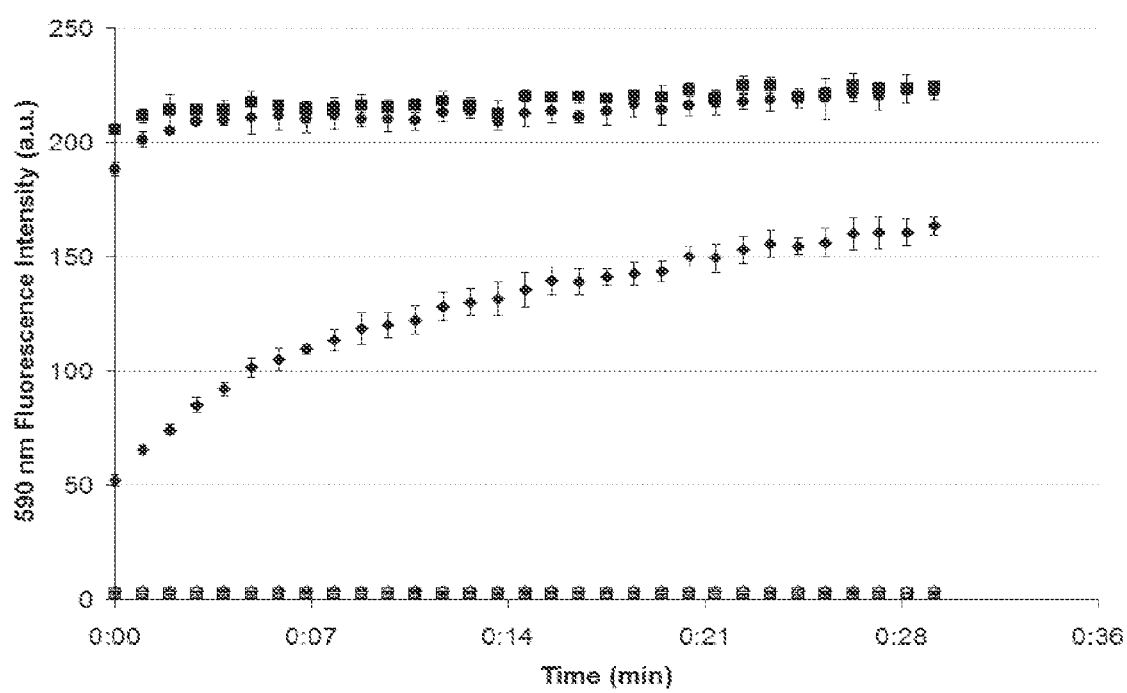

FIG. 2 provides data demonstrating that 1 mM EDTA appears to have an inhibitory effect on DNase I activity using the DNaseALERT™ assay. DNaseALERT™ substrate fluorescence of Buffer A with EDTA (♦, diamonds), Buffer A without EDTA (●, circles), and DNase I buffer (■, squares). The controls without DNase I are shown using empty diamonds, circles and squares and are clustered at the baseline.

Figure 3:
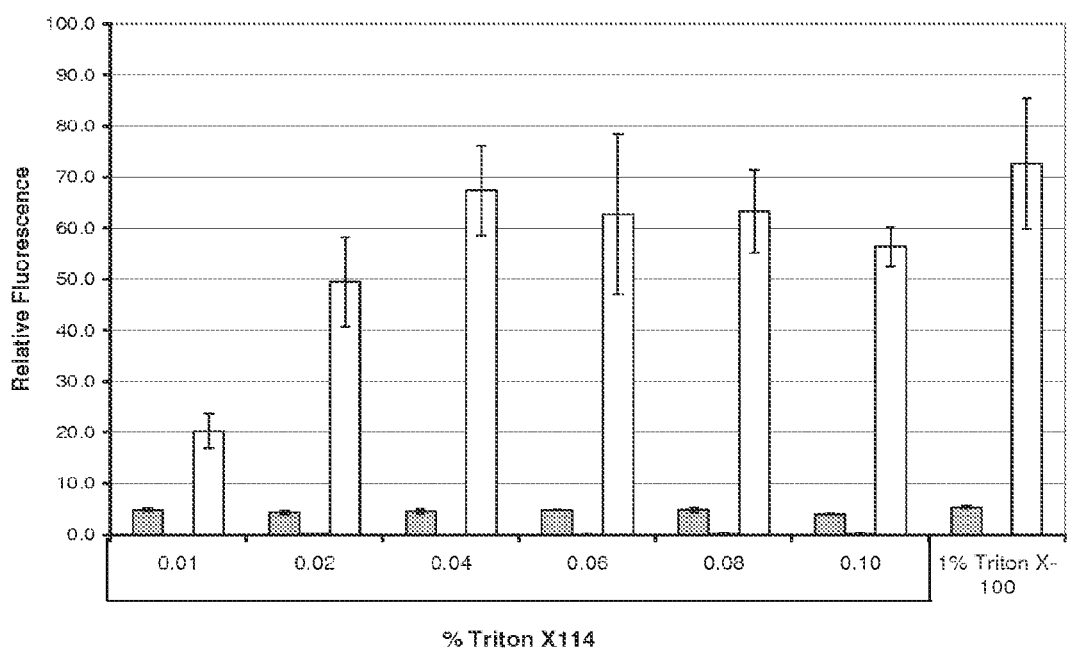

FIG. 3 provides data on cell lysis using TRITON X-114™ surfactant at six different concentrations and using TRITON X-100™ surfactant at one concentration as determined by propidium iodide (PI) staining (1 mg/ml) of $10^5$ HeLa cells. Shown are fluorescence intensities of mixtures containing buffer and PI (shaded bars), buffer and cells (cross-hatched bars (all are at the baseline)), and buffer and cells and PI (empty bars).

Figure 4:
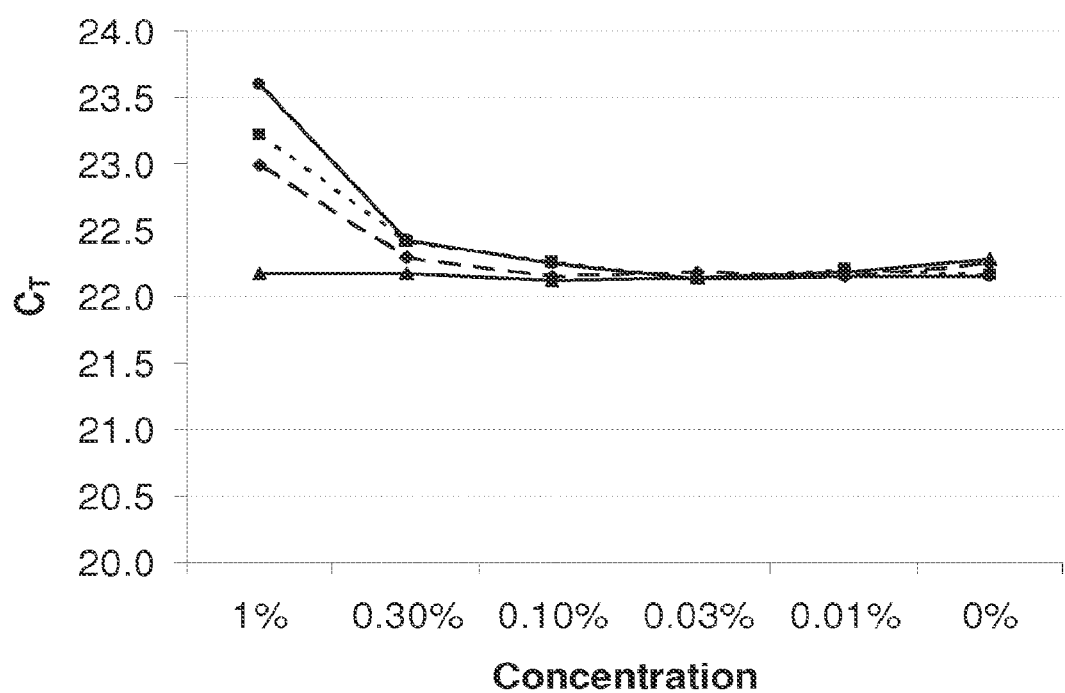

FIG. 4 provides data on the concentration of four separate surfactants versus cycle threshold using PCR and PPIA (peptidylprolyl isomerase A) as described in Example 2. Data are provided for TRITON X-114™ (triangles, solid line), THESIT™ (diamonds, dashed line), TRITON X-100™ (squares, dotted line), and NONIDET P-40™ (circles, solid line) surfactants.

Figure 5:
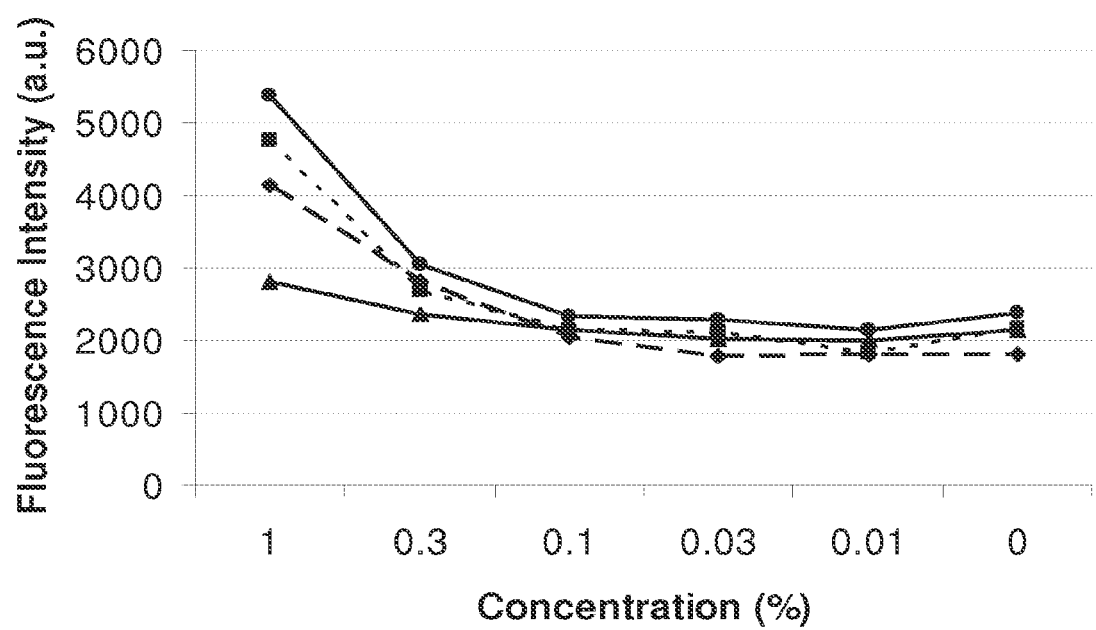

FIG. 5 provides data on 5-carboxyfluorescein (5-FAM™) background fluorescence at different concentrations for four different surfactants. Data are provided for TRITON X-114™ (triangles, solid line), THESIT™ (diamonds, dashed line), TRITON X-100™ (squares, dotted line), and NONIDET P-40™ (circles, solid line) surfactants.

Figure 6A:
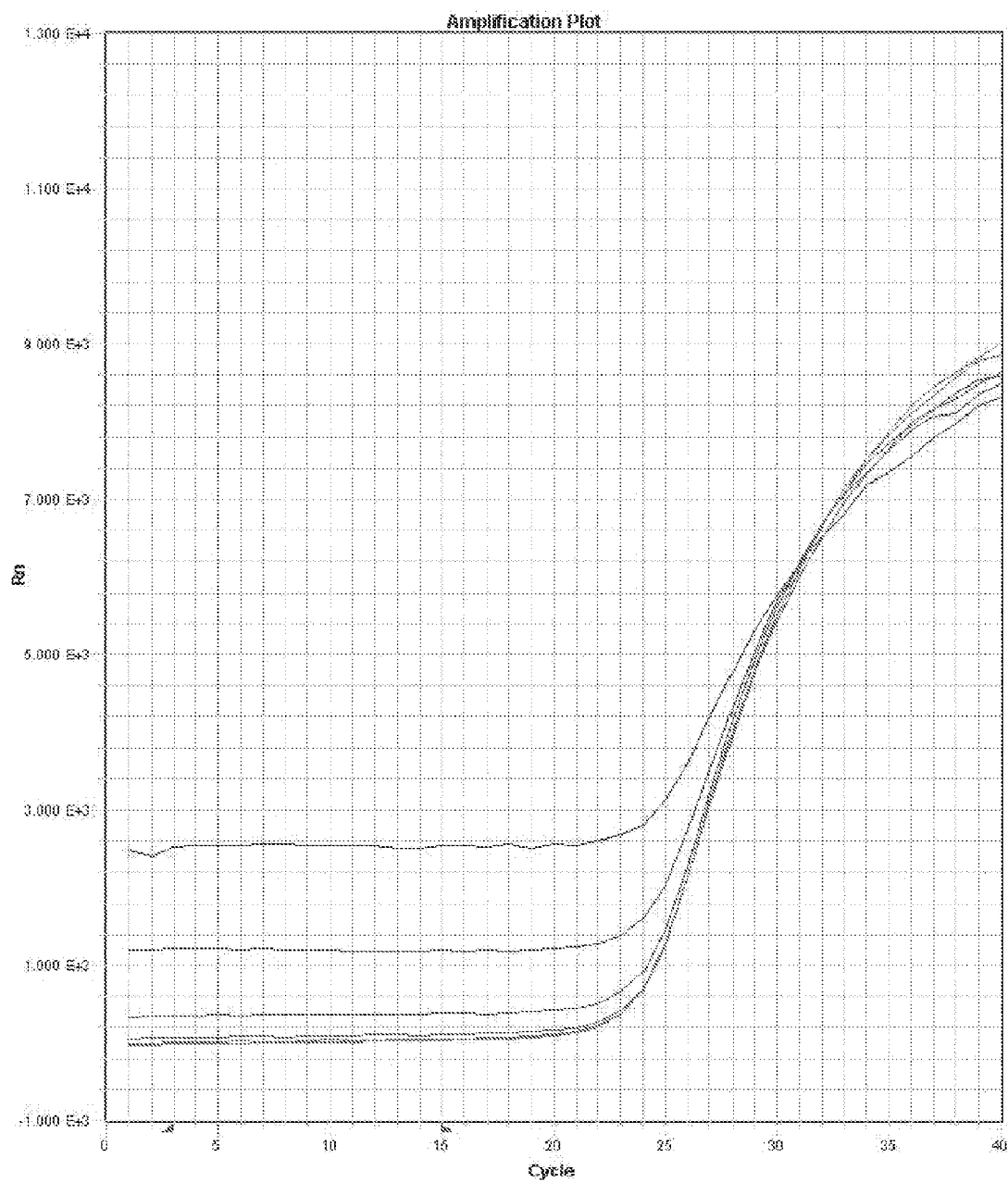
Figure 6D:
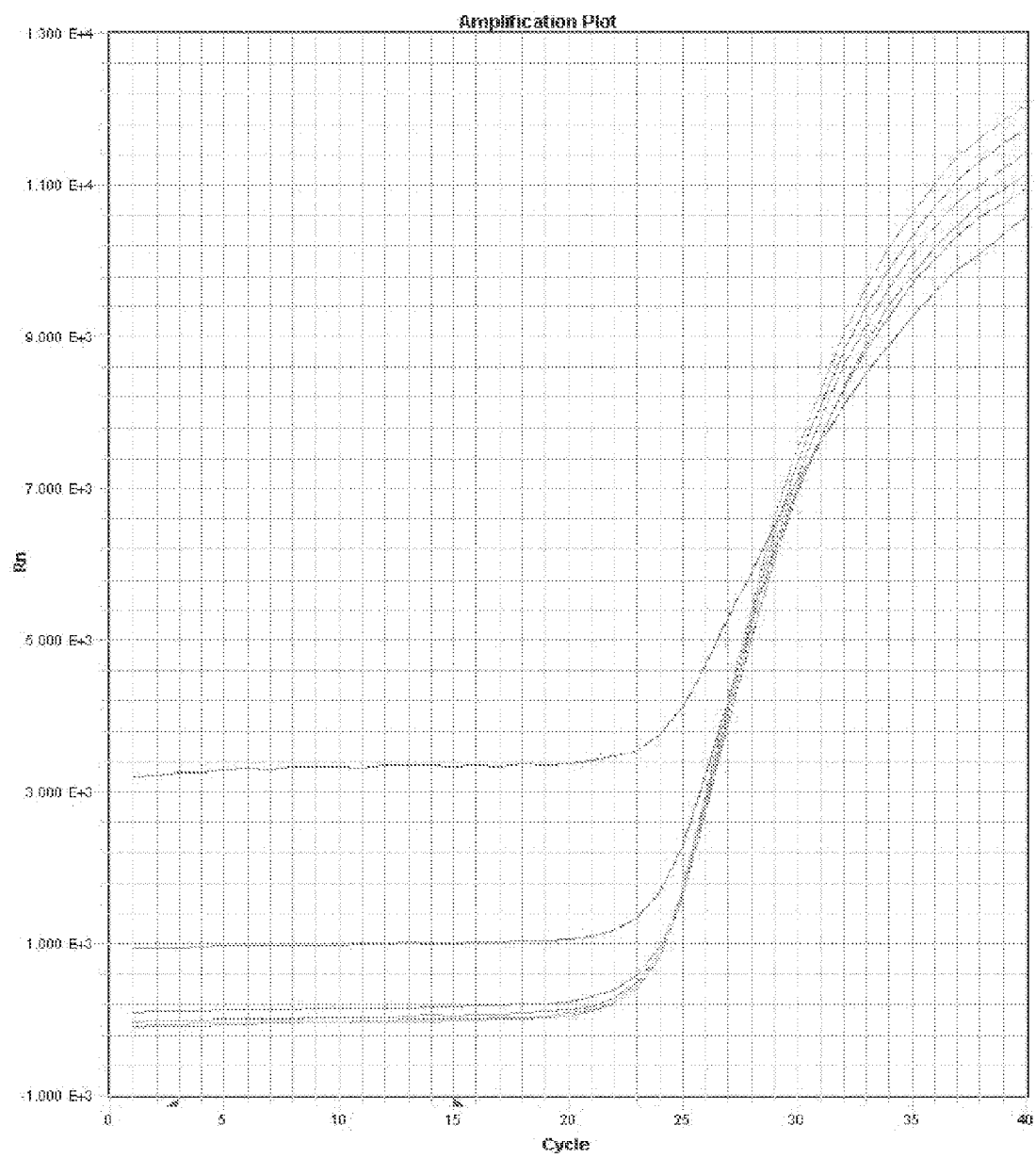

FIG. 6A-FIG. 6D provide amplification plots of Rn (fluorescence corrected to a reference ROX™ dye) vs cycle number in the presence of THESIT™ (FIG. 6A), TRITON X-100™ (FIG. 6B), TRITON X-114™ (FIG. 6C) and NONIDET P-40™ (FIG. 6D). Concentrations of surfactants are as for FIG. 4 and FIG. 5.

Figure 7:
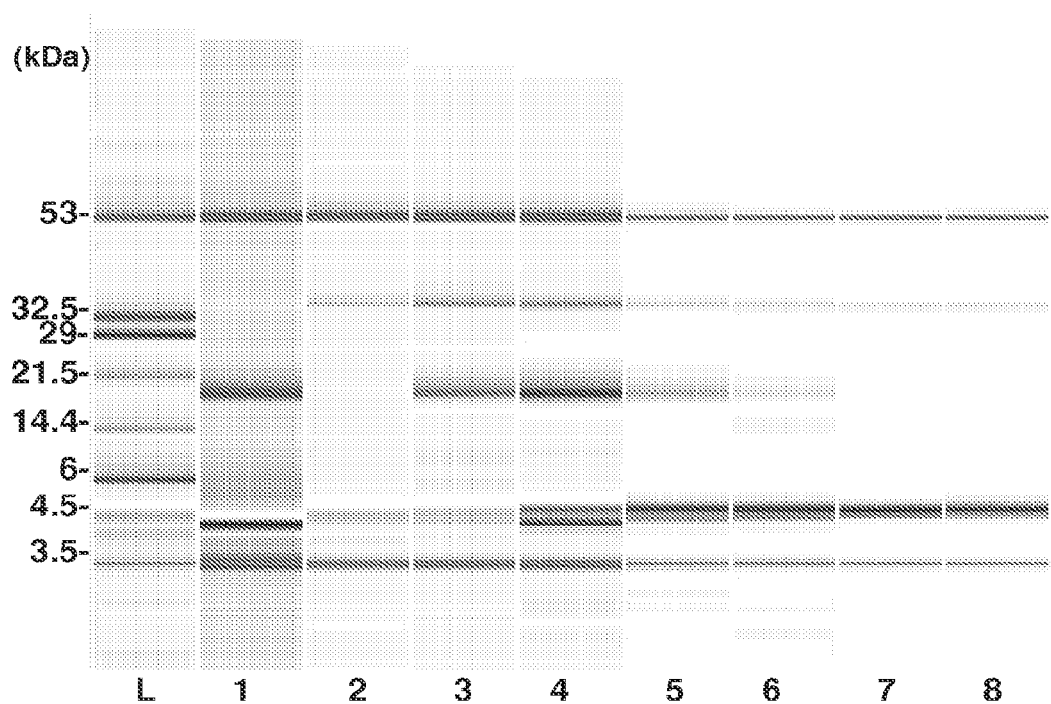

FIG. 7 provides an analysis of proteinase K inhibition by methoxysuccinyl-Ala-Ala-Pro-Val-chloromethyl ketone (AAPV, SEQ ID NO:1) for isothermal preparation of samples for processing of nucleic acid. The lower marker is at about 3.5 kDa; the next higher prominent bands are system peaks at about 4.0-4.5 kDa; intact RNase A is at about 20 kDa; and proteinase K is at about 35 kDa. Lanes are labeled as follows: (L) Ladder, (1) RNase Only, (2) PK Only, (3)-(8) AAPV (SEQ ID NO:1) at 1 mM (3), 0.75 mM (4), 0.5 mM (5), 0.25 mM (6), 0.125 mM (7), and 0 mM (8).

Figure 8:
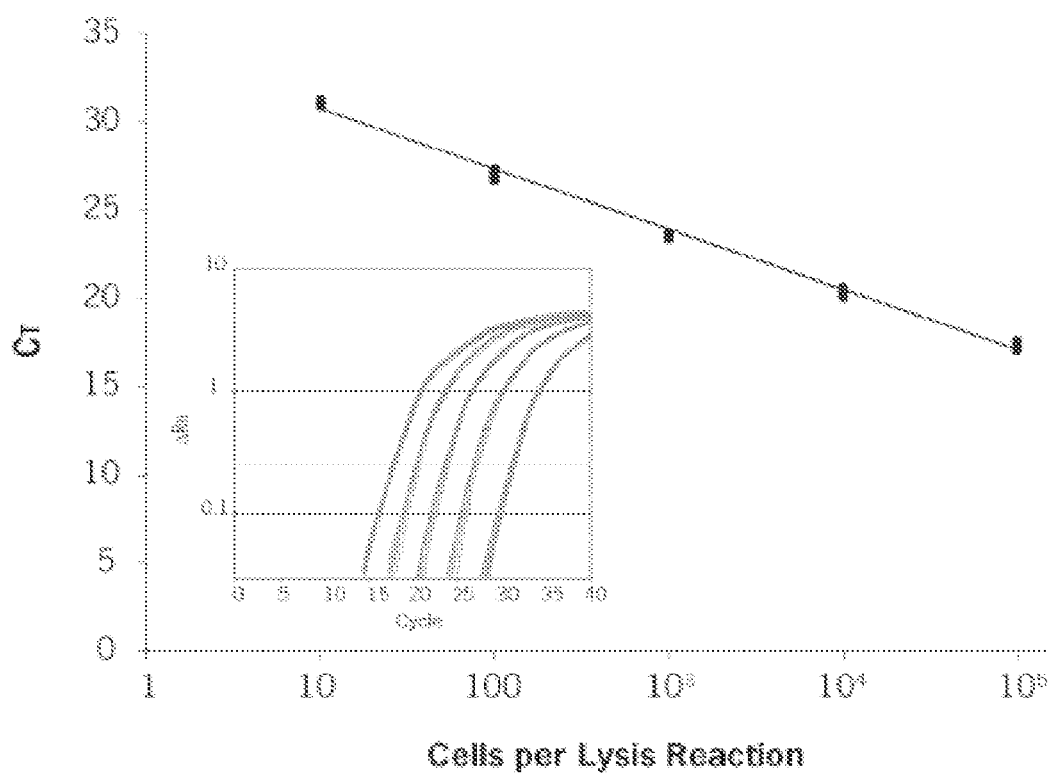

FIG. 8 provides data showing results from sample processing of HeLa cells (10-$10^5$ cells per lysis reaction) and analysis using a TAQMAN® Gene Expression Assay for β-actin. There is good linearity down to an input of as few as 10 cells. (Slope=−3.41, $R^2$=1).

Figure 9A:
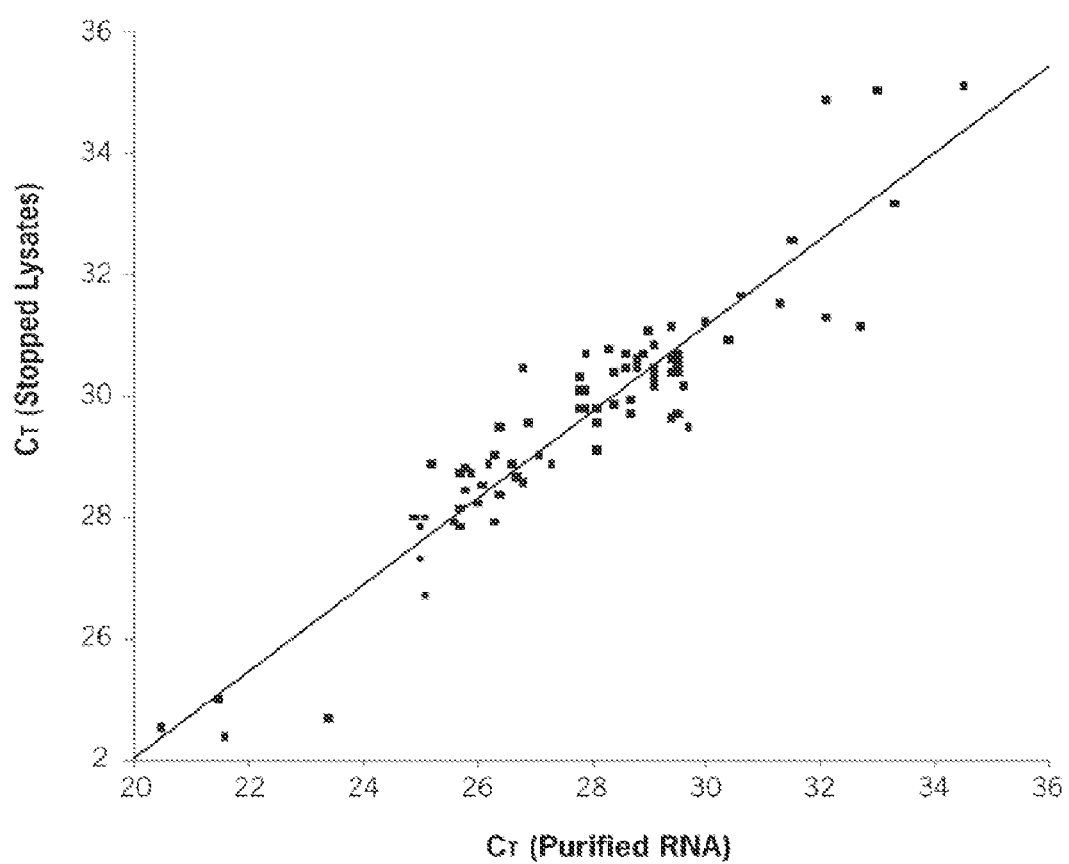
Figure 9B:
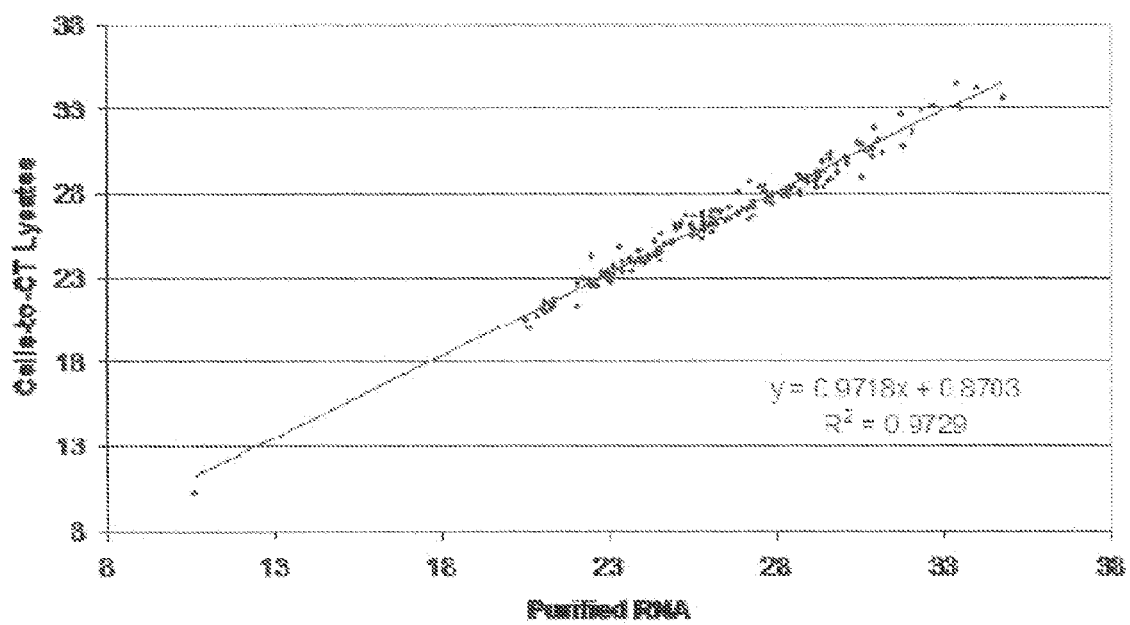

FIG. 9A-FIG. 9B demonstrate that $C_T$ values obtained using lysates as prepared using processes provided herein were found to be essentially equivalent to $C_T$ values obtained with purified RNA.

Figure 10:
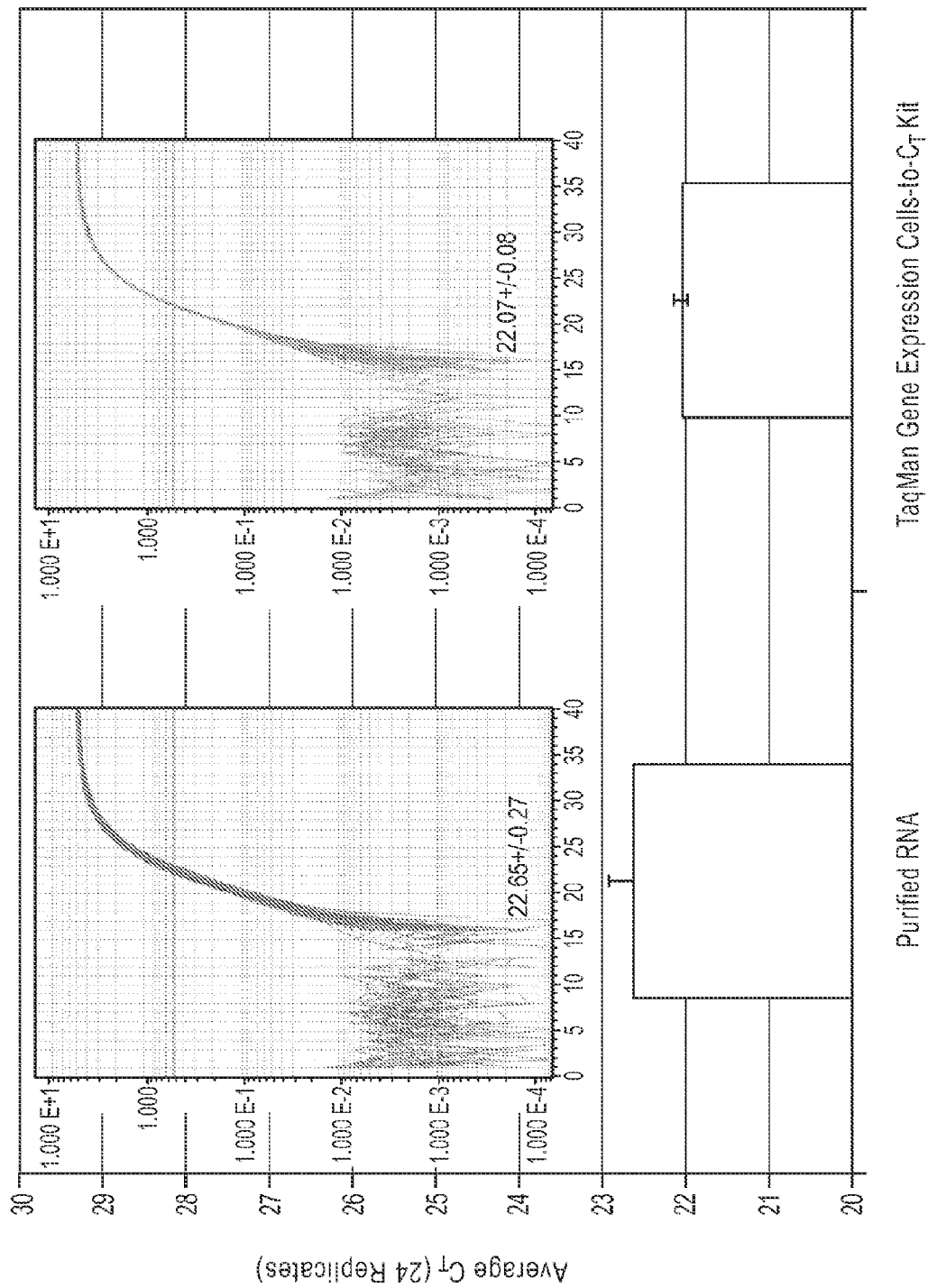

FIG. 10 provides data demonstrating the reproducibility of samples prepared according to embodiments herein as compared to purified RNA. 24 replicates of 5000 HeLa cells were either subjected to traditional RNA purification or cell lysis using isothermal preparation methods of teachings herein. Samples were then evaluated using a TAQMAN® Gene Expression Assay for β-actin.

Figure 11:
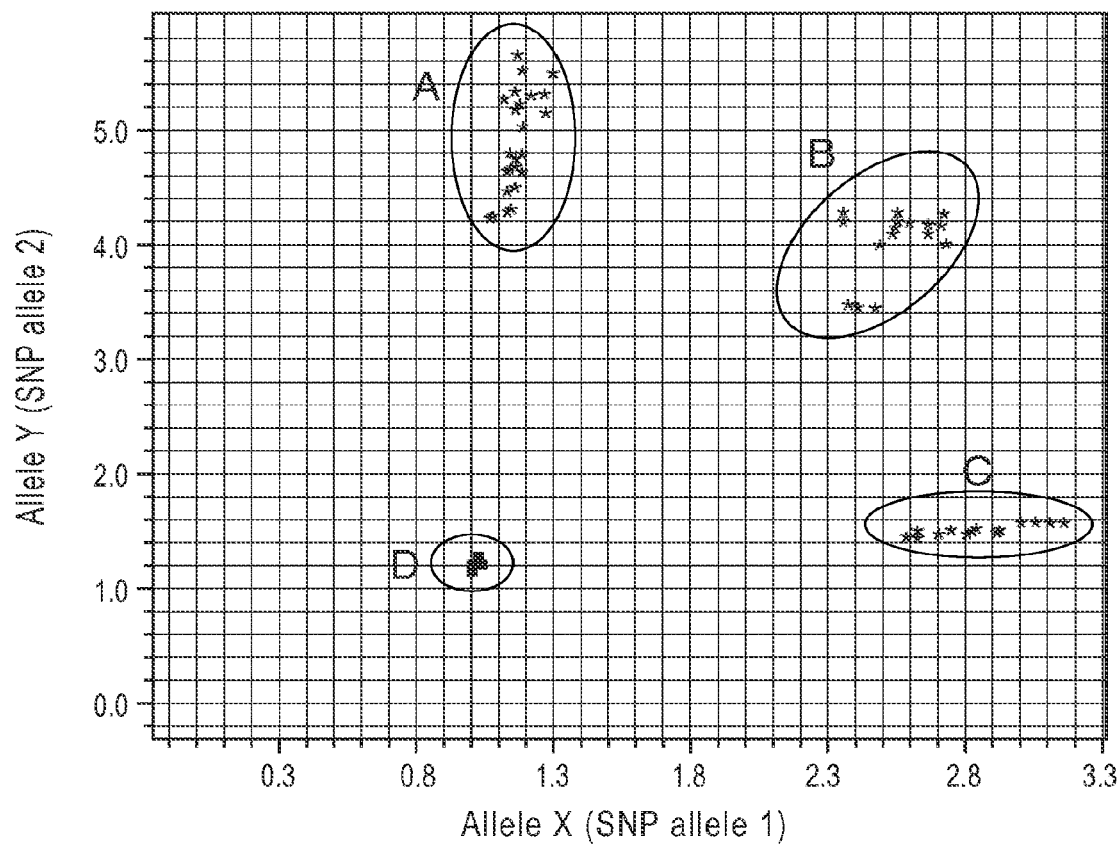

FIG. 11 provides data for detection of SNPs using sample preparation processes of embodiments herein as compared to using purified DNA from the same cell sources. The data are clustered for cell lines with allele Y at "A," for cell lines with allele X at "C" and for cell lines containing both alleles at "B" thereby showing consistency of results from the two methods. The "D" data provide the no template control samples.

DESCRIPTION OF VARIOUS EMBODIMENTS

It is to be understood that both the foregoing general description and the following detailed description are exemplary and explanatory only and are not intended to limit the scope of the current teachings. In this application, the use of the singular includes the plural unless specifically stated otherwise. The use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y." As used herein and unless otherwise indicated, the terms "a" and "an" are taken to mean "one," "at least one" or "one or more."

Whenever a range of values is provided herein, the range is meant to include the starting value and the ending value and a value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Temperature: The sample preparation processes of teachings herein include a contacting step to produce a lysate and an admixing step where the lysate is mixed with a stop mixture where the steps are carried out at substantially the same temperature. "Substantially the same temperature" generally refers to an isothermal process of holding the temperature relatively constant during the contacting and admixing steps and, for certain embodiments described herein, means ambient temperature which temperature may change during the day or from lab to lab. In general, the contacting and admixing steps are carried out at substantially the same temperature, which temperature is about 15° C. to 40° C., or about 16° C. to 28° C. or about 19° C. to 26° C., or about 19° C. to 25° C., or about 22° C. to 25° C., or at ambient temperature, or about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. An isothermal process is particularly amenable for high throughput analyses.

Sample: The term "sample," as used herein, refers to an in vitro cell, cell culture, virus, bacterial cell, fungal cell, plant cell, bodily sample, or tissue sample that contains genetic material. In certain embodiments, the genetic material of the sample comprises RNA. In other embodiments, the genetic material of the sample is DNA, or both RNA and DNA. In certain embodiments, a tissue sample includes a cell isolated from a subject. A subject includes any organism from which a sample can be isolated. Non-limiting examples of organisms include prokaryotes, eukaryotes or archaebacteria, including bacteria, fungi, animals, plants, or protists. The animal, for example, can be a mammal or a non-mammal. The mammal can be, for example, a rabbit, dog, pig, cow, horse, human, or a rodent such as a mouse or rat. In particular aspects, the tissue sample is a human tissue sample. The tissue sample can be, for example, a blood sample. The blood sample can be whole blood or a blood product (e.g., red blood cells, white blood cells, platelets, plasma, serum). The sample, in other non-limiting embodiments, can be saliva, a cheek, throat, or nasal swab, a fine needle aspirate, a tissue print, cerebral spinal fluid, mucus, lymph, feces, urine, skin, spinal fluid, peritoneal fluid, lymphatic fluid, aqueous or vitreous humor, synovial fluid, tears, semen, seminal fluid, vaginal fluids, pulmonary effusion, serosal fluid, organs, bronchio-alveolar lavage, tumors, frozen cells, or constituents or components of in vitro cell cultures. In other aspects, the tissue sample is a solid tissue sample or a frozen tissue sample. In still further aspects, the sample comprises a virus, bacteria, or fungus. The sample can be an ex vivo tissue or sample or a sample obtained by laser capture microdissection. The sample can be a fixed sample, including as set forth by U.S. Published Patent Application No. 2003/0170617 filed Jan. 28, 2003.

Sample preparation processes provided by teachings herein are for from one cell up to about $10^5$-$10^6$ cells per sample or any range therebetween. For certain cell lines, such as HeLa cells, linear $C_T$ values were obtained for up to $10^6$ cells per sample preparation. A patient needle biopsy often consists of thousands of cells. A biopsy could be prepared using methods herein, PCR amplified and analyzed by measuring the expression of certain genes, for example.

In some embodiments, the sample is removed from serum components prior to preparation. In some embodiments, the sample is washed with a solution comprising, for example, but not limited to, phosphate-buffered saline (PBS), physiological saline, serum-free media or suitable solution with appropriate tonicity.

In situ analysis of genetic material or a surrogate thereof: The term "in situ analysis," as used herein means that processes provided herein allow DNA or RNA analysis to be carried out in the same tube or on an aliquot of the stopped mixture without centrifugation or extraction. That is, RNA or DNA need not be isolated from the stopped mixture prior to mixing at least a portion of the stopped mixture with a composition comprising reverse transcriptase or another relevant enzyme. The term "or a surrogate thereof," as used herein means a detectable product that represents the RNA or DNA present in the sample, such as an amplified product of the RNA or DNA.

Lysis Mixture: A "lysis mixture," as used herein, comprises components for isothermally lysing a sample and lacks components that can interfere with later detection of DNA or RNA, or a surrogate thereof, using emission detection at wavelengths of 300 nm to 750 nm. A lysis mixture for RNA analysis comprises a lysis solution and a polypeptide having deoxyribonuclease activity. A lysis mixture for DNA analysis lacks a polypeptide having deoxyribonuclease activity and may contain, in some embodiments, a polypeptide having ribonuclease activity. A lysis reaction is a lysis mixture combined with a sample. Incubation of a lysis reaction can be for any range of time between 2 minutes to about 30 minutes, about 2 minutes to about 20 minutes, about 3 minutes to about 15 minutes, about 4 minutes to about 10 minutes, about 8 minutes, about 7 minutes, about 6 minutes, or about 5 minutes.

A lysis solution comprises, for certain embodiments herein, a Tris-base or Tris-Cl buffer at a pH of about 7.5 to about 8.2 for a range of temperatures such as 19° C. to 25° C., a polypeptide having protease activity, and a surfactant that substantially lacks fluorescence between 300 nm and 750 nm. The lysis solution is used at a lysis-effective concentration. Further, the lysis solution is substantially free of a cation chelator.

A Polypeptide having Protease Activity: In certain embodiments herein, the lysis solution comprises a polypeptide having protease activity such as for example, proteinase K. In lieu of, or in addition to, proteinase K, the lysis solution can comprise a serine protease such as trypsin, chymotrypsin, elastase, subtilisin, streptogrisin, thermitase, aqualysin, plasmin, cucumisin, or carboxypeptidase A, D, C, or Y; a cysteine protease such as papain, calpain, or clostripain; an acid protease such as pepsin, chymosin, or cathepsin; or a metalloprotease such as pronase, thermolysin, collagenase, dispase, an aminopeptidase or carboxypeptidase A, B, E/H, M, T, or U.

A surfactant that substantially lacks fluorescence between 300 nm and 750 nm when in use for in situ analysis of DNA, RNA or a surrogate thereof: In embodiments provided herein, the lysis solution comprises a surfactant at a concentration that has low or no emission at the emission wavelengths of dyes or labels commonly used for detecting RNA or DNA when in use for in situ analysis of DNA, RNA or a surrogate thereof.

A lysis-effective concentration of surfactant in a lysis mixture is a concentration of surfactant at which a sample is considered fully lysed as determined by propidium iodide staining using 1% TRITON X-100™ surfactant as a control. Lysis-effective concentrations of exemplary surfactants range from 0.02% or 0.05% to 3% or more for TRITON X114™ surfactant, from 0.01% or 0.05% to 5% or more for THESIT™ surfactant, from 0.1% to 5% or more for NONIDET P-40™ surfactant, and from 0.05% to 1% or to 3% for TRITON X-100™ surfactant. When a combination of surfactants is used, the concentration of each surfactant may be lowered from the cited amounts.

For the methods and processes described herein, the lysate is diluted when stop solution is added. The stopped mixture is further diluted when a portion is transferred to a RT-qPCR reaction. The concentration of surfactant in the qPCR reaction is thereby diluted when compared to the concentration of the surfactant in the lysate. The dilution factor may range from a 1.25-fold dilution to a thousand-fold or more dilution. Concentrations of the above-listed surfactants that, in addition to being lysis-effective, have low or no emission at the emission wavelengths of green emitters (500 nm to 549 nm) when in use for in situ analysis of RNA or a surrogate thereof include TRITON X-114™ surfactant at 0.05% to 1%; THESIT™ surfactant at 0.05% to 0.3%; TRITON X-100™ surfactant at 0.05% to 0.3%; NONIDET P-40™ surfactant at 0.1% to 0.3%, or a combination thereof. Commonly used labeling dyes having emission wavelengths of green emitters include FAM™ dye, FITC, and JOE™ dye.

A polypeptide having deoxyribonuclease activity: A polypeptide having deoxyribonuclease activity is present in certain lysis mixtures as set forth in embodiments herein where RNA is to be detected. The polypeptide having deoxyribonuclease activity is dependent upon cations such as $Ca^{++}$ or $Mg^{++}$ for stability and activity. In the case where a polypeptide having deoxyribonuclease activity is obtained with a cation already present, which is commonly the case, additional cations are not needed in the lysis mixture. In the case where a polypeptide having deoxyribonuclease activity is obtained lacking cations, exogenous cations are added to the lysis mixture. A polypeptide having deoxyribonuclease activity can be DNase I or Nuclease BAL-31, both of which are $Ca^{++}$- and $Mg^{++}$-dependent; or exonuclease I, exonuclease III, Lambda exonuclease, CviKI-1 endonuclease, or McrBC endonuclease, all of which are $Mg^{++}$-dependent, or an enzymatically active mutant or variant thereof. A polypeptide having deoxyribonuclease activity can be present in the lysis mixture from 100 U/ml to 600 U/ml in some embodiments and, for other embodiments, about 200 U/ml, about 300 U/ml, about 400 U/ml, about 500 U/ml or any range of concentrations therebetween.

Substantially free of a cation chelator: In general, the lysis mixtures for RNA sample preparation processes are substantially free of a cation chelator. A common cation chelator, such as EDTA, has been found herein to interfere with deoxyribonuclease activity at a concentration of 1 mM. Therefore, lysis mixtures provided herein for RNA sample preparation are substantially free of a cation chelator, have less than about 0.1 mM cation chelator, have less than about 0.2 mM cation chelator, have less than about 0.5 mM or have less than 1 mM cation chelator.

Optional Lysis Mixture ingredients: In some embodiments, a calcium salt is present in the lysis mixture in concentrations ranging from 0 mM to 2.5 mM for stabilizing a deoxyribonuclease. The calcium salt can be any calcium salt that provides such function and can be calcium chloride, calcium bromide, calcium acetate, calcium formate, calcium sulfate, or calcium phosphate, for example. In certain embodiments, the calcium salt is $CaCl_2$ and the $CaCl_2$ is present at about 0.1 mM, 0.2 mM, 0.5 mM, 1.0 mM, or 2.0 mM or any range of concentrations therebetween. In some embodiments, $MgCl_2$ is present in the lysis solution in concentrations ranging from 0 mM to 2.5 mM. In certain embodiments, the $MgCl_2$ is present at about 0.5 mM, 1.0 mM, 1.5 mM, 2.0 mM, or 2.5 mM or any range of concentrations therebetween. Certain assays such as short tandem repeat detection assays use lower concentrations of $MgCl_2$ such as about 0.5 mM.

In some embodiments, the lysis mixture comprises at least one reducing agent. Use of reducing agents is well known by those of ordinary skill in the art. Exemplary reducing agents include dithiothreitol, β-mercaptoethanol, dithioerythritol, or combinations thereof.

In some embodiments, addition of a reducing agent at a final concentration of about 0.01 mM in the lysis mixture together with addition to the stop solution (as discussed below) improves cycle threshold values.

In some embodiments, the lysis mixture further comprises at least one additional catabolic enzyme. For example, a glycoside hydrolase such as amylase, lysozyme or cellulase can be included for degradation of polysaccharides, or lipase may be included for degradation of lipids, or a combination thereof may be used. In such cases, it may be necessary to balance the concentration, reaction conditions, or timing of addition of one or more catabolic enzymes, in order to prevent degradation of the at least one additional catabolic enzyme by the protease. Such reaction optimization is well within the skill of those of ordinary skill in the art in light of the teachings herein.

Exemplary non-limiting embodiments of lysis mixtures are prepared by obtaining stock solutions of 1M Tris-base pH 8.0, 1M $MgCl_2$, 1M $CaCl_2$, 1M DTT, proteinase K at 20 mg/ml, 20% TRITON X114™ and nuclease-free water. Stock solutions are diluted to form a lysis solution of Tris pH 8.0, 10 mM; $MgCl_2$, 0.5 mM; $CaCl_2$, 0.5 mM; a reducing agent such as DTT, β-mercaptoethanol or dithioerythritol, 0.01 mM; protease such as proteinase K, 100 ug/ml; and TRITON X114™, 0.1%, in nuclease free water. The pH is adjusted to pH 7.8 +/−0.1 with HCl at a temperature of 19° C.-25° C. (a range of pH values is about pH 7.5 to about pH 8.2). The lysis solution can be stored at −20° C., at 4° C., and has been found to be stable at 25° C. for one year. In some embodiments, lysis can be carried out in a 50 uL volume at a pH of about 7.8.

Stop Mixture: In some embodiments, a stop mixture comprises a cation chelator effective to inactivate the polypeptide having deoxyribonuclease activity of the lysis mixture, an inhibitor of the polypeptide having protease activity of the lysis mixture, and generally, a stop mixture comprises a Tris-base or Tris-Cl buffer at about pH 8. For analysis embodiments by RT-PCR, the stopped mixture is compatible with reverse transcriptase and DNA polymerase reaction conditions. A stopped mixture can be included in such reactions up to 45% or up to 65% or more of the RT or PCR reaction volume depending upon the concentrations of the various components.

A cation chelator effective to inactivate the polypeptide having deoxyribonuclease activity of the stop mixture: For embodiments where the polypeptide having deoxyribonuclease activity is dependent upon calcium ions for stability and activity, the cation chelator comprises a calcium chelator such as EGTA, EDTA, or citrate, for example. For embodiments where the polypeptide having deoxyribonuclease activity is dependent upon magnesium ions for stability and activity, the cation chelator comprises a magnesium chelator such as EDTA, for example. Of course, divalent cation chelators bind a variety of divalent cations and overlap in specificity for divalent cations is expected. Cation chelators include EGTA, ethylenediamine tetraacetic acid (EDTA), sodium citrate, cation exchange beads such as SP SEPHAROSE™ beads (GE Healthcare), 1,10-phenanthroline, tetrakis-(2-pyridylmethyl)ethylenediamine (TPEN), 1,2-bis(2-aminophenoxy)ethane-N,N,N',N'-tetraacetic acid (BAPTA), or a combination thereof. EGTA inhibits DNase I at ≥4 mM and is compatible with RT-PCR.

An inhibitor of the polypeptide having protease activity: The stop mixture comprises a chemical or molecular inhibitor of the polypeptide having protease activity. In addition, the inhibitor has essentially no inhibitory effect on reverse transcriptase or on DNA polymerase.

For some embodiments where the polypeptide having protease activity is proteinase K, the chemical inhibitor comprises a methoxysuccinyl-Ala-Ala-Pro/Leu-Ala/Val-haloalkyl ketone (SEQ ID NO:2) where the halo is chloro, fluoro, iodo or bromo and the alkyl is $C_1$ to $C_3$ or active derivatives or analogs thereof. In certain embodiments, the chemical inhibitor comprises methoxysuccinyl-Ala-Ala-Pro/Leu-Ala/Val-chloroalkyl ketone (SEQ ID NO:2) where the alkyl is $C_1$ to $C_3$ or active derivatives or analogs thereof. Methoxysuccinyl-AAPV-chloromethyl ketone (SEQ ID NO:1) (Bachem, Torrance, Calif., or, for example, in DMSO, Sigma-Aldrich, St. Louis, Mo.) at a concentration as low as 0.75 mM was demonstrated to have inhibitory activity for 100 μg/ml PK and is compatible with both one-step and two-step RT-PCR reactions.

Other inhibitors of proteinase K include carbobenzoxy-Ala-Ala-COCH$_2$Cl, carbobenzoxy-Ala-Ala-Phe-COCH$_2$Cl or carbobenzoxy-Phe-Pro-Arg-COCH$_2$Cl as described by Wolf et al. (*JBC* 266:26, 17695, 1991), and phenylmethylsulfonyl fluoride (PMSF). In some embodiments, PMSF is present at a concentration of up to 2 mM in the stopped mixture or up to 400 uM in an RT reaction. Further inhibitors of the polypeptide having protease activity include the proline-containing tetrapeptide derivatives and proline-containing tripeptide derivatives of U.S. Pat. No. 4,596,789 (application Ser. No. 603,408 filed Apr. 24, 1984) and U.S. Pat. No. 4,691,007 (application Ser. No. 806,265 filed Dec. 6, 1985) issued Jun. 24, 1986 and Sep. 1, 1987, respectively, to Anand S. Dutta et al., including acid- and base-addition salts thereof; the peptide derivatives of U.S. Pat. No. 4,910,190 (application Ser. No. 5,538 filed Jan. 20, 1987) and issued Mar. 20, 1990 to Bergeson et al. including salts thereof; the peptide derivatives of U.S. Pat. No. 5,414,132 (application Ser. No. 940,932 filed Sep. 4, 1992) issued May 9, 1995, and U.S. Pat. No. 5,907,068 (application Ser. No. 07/941,001 filed Sep. 4, 1992) issued May 25, 1999, both to Stein et al. including salts thereof; and the peptide derivatives of U.S. Pat. No. 5,055,450 (application Ser. No. 493,025 filed Mar. 13, 1990) issued Oct. 8, 1991, and U.S. Pat. No. 5,726,158 (application Ser. No. 467,333 filed Jun. 6, 1995) issued Mar. 10, 1998, both to Edwards et al. including salts thereof.

Further protease/protease inhibitor pairs include leupeptin as an inhibitor for serine and cysteine proteases such as plasmin, trypsin, papain, kallikrein and cathepsin B; 4-(2-aminoethyl)benzenesulfonyl fluoride (AEBSF) as an inhibitor for serine proteases such as chymotrypsin, kallikrein, plasmin, thrombin, and trypsin; aprotinin as an inhibitor of serine proteases such as trypsin, chymotrypsin, plasmin and kallikrein; benzamidine as an inhibitor of trypsin; N-acetyl eglin-C as an inhibitor of chymotrypsin, subtilisin, leukocyte elastase and cathepsin G; and antipain or plasmin for inhibition of a serine or cysteine such as papain and trypsin.

Further protease inhibitors include aptamers, or polyclonal or monoclonal antibodies having binding affinity and binding specificity for the polypeptide having protease activity of the lysis mixture.

Optional Stop Mixture Ingredients: In some embodiments, the stop mixture comprise one or more ribonuclease inhibitors such as placental ribonuclease inhibitor protein (RIP, Promega, Madison, Wis.) at about 0.2 U/uL to about 0.002 U/ul, SUPERase-In™ (protein-based inhibitor for RNase A, B, C, 1, and T1, Catalog No. AM2694, AMBION®, Austin, Tex.), RNase inhibitor (a recombinant human placental protein having inhibitory activity for neutral pancreatic RNase A-type enzymes, Catalog No. AM2682, AMBION®, Austin, Tex.) and anti-RNase A (protein-based inhibitor for RNase A, Catalog No. AM2690, AMBION®, Austin, Tex.). The addition of RIP reduces PCR cycle threshold values at 30 min for both 5000 and 100,000 cell samples. Final RIP concentration (0.2 U/ul, after addition to lysate; 2.2 U/uL in the stop solution) helps prevent RNA degradation, particularly if the lysate is allowed to sit at room temperature for longer than about 20 minutes.

As recited supra, addition of a reducing agent to the stop solution at 0.11 mM improved cycle threshold results for PCR at 10 minutes post-stop. While not wanting to be bound by theory, a reducing agent is provided for the stop solution to improve functionality and stability of ribonuclease inhibitor protein (RIP).

A stop reaction is incubated for up to 2 minutes. After about 20 minutes, PCR cycle threshold values increase very gradually. In some embodiments, a stopped mixture has a pH of 7.3-7.8 as a result of the protease inhibition reaction.

Detection of DNA, RNA or a surrogate thereof: Embodiments of detecting DNA, RNA or a surrogate thereof in a stopped mixture as provided herein includes detection means using emission by an emitter that is representative of the RNA or DNA in the stopped mixture.

In some embodiments, RNA of a stopped mixture as provided by teachings herein is detected in situ by adding or mixing at least a portion of the stopped mixture with a composition comprising reverse transcriptase to form a reverse transcriptase reaction mixture. A reverse transcription reaction provides a surrogate of the RNA that can be detectable. Any reverse transcriptase known to those of ordinary skill in the art can be used such as, for example, MMLV-RT (murine maloney leukemia virus-reverse transcriptase), avian myelogenous virus reverse transcriptase (AMV-RT), human immunodeficiency virus (HIV)-RT and the Tth DNA polymerase which has reverse transcriptase activity if $Mn^{++}$ is provided.

A positive control for detection of RNA or DNA can be a non-homologous RNA random sequence such as XENO™RNA (Applied Biosystems, Foster City, Calif.). A control for qPCR can be a β-actin probe/primer set, also available from Applied Biosystems, for example. The positive control can be mixed with the stop solution and therefore is added at the time of adding stop solution to a sample.

Amplification: As used herein, "amplification" or "amplify" and the like refers to a process that results in an increase in the copy number of a molecule or set of related molecules. As the term applies to a stopped mixture herein, amplification means the production of multiple copies of the target nucleic acid, a surrogate of a target nucleic acid, or a portion thereof. Amplification can encompass a variety of chemical and enzymatic processes such as a polymerase chain reaction (PCR), a strand displacement amplification reaction, a transcription mediated amplification reaction, or a nucleic acid sequence-based amplification reaction, for example. Following at least one amplification cycle, the amplification products can be detected or can be separated from at least one other component of the amplification mixture based on their molecular weight or length or mobility prior to detection.

Polymerase Chain Reaction: PCR includes introducing a molar excess of two or more extendable oligonucleotide primers to a reaction mixture comprising the stopped mixture where the primers hybridize to opposite strands of a DNA, RNA or RNA surrogate. The reaction mixture is subjected to a program of thermal cycling in the presence of a DNA polymerase, resulting in the amplification of the DNA or RNA surrogate sequence flanked by the primers. Reverse transcriptase PCR is a PCR reaction that uses an RNA template and a reverse transcriptase, or a polypeptide having reverse transcriptase activity, to first generate a single stranded DNA molecule prior to the multiple cycles of DNA-dependent DNA polymerase primer elongation as cited above. Methods for a wide variety of PCR applications are widely known in the art, and described in many sources, for example, Ausubel et al. (eds.), Current Protocols in Molecular Biology, Section 15, John Wiley & Sons, Inc., New York (1994).

Criteria for designing sequence-specific primers are well known to persons of ordinary skill in the art. Detailed descriptions of primer design that provide for sequence-specific annealing can be found, among other places, in Diffenbach and Dveksler, PCR Primer, A Laboratory Manual, Cold Spring Harbor Press, 1995, and Kwok et al. (*Nucl. Acid Res.* 18:999-1005, 1990). The sequence-specific portions of the primers are of sufficient length to permit specific annealing to complementary sequences, as appropriate. A primer does not need to have 100% complementarity with a primer-specific portion for primer extension to occur. Further, a primer can be detectably labeled such that the label is detected by spectroscopy. A primer pair is sometimes said to consist of a "forward primer" and a "reverse primer," indicating that they are initiating nucleic acid polymerization in opposing directions from different strands of a duplex template.

In some embodiments, a primer as set forth herein can comprise a universal priming sequence. The term "universal primer" refers to a primer comprising a universal sequence that is able to hybridize to all, or essentially all, potential target sequences in a multiplexed reaction. The term "semi-universal primer" refers to a primer that is capable of hybridizing with more than one (e.g., a subset), but not all, of the potential target sequences in a multiplexed reaction. The terms "universal sequence," "universal priming sequence" or "universal primer sequence" or the like refer to a sequence contained in a plurality of primers, where the universal priming sequence that is found in a target is complementary to a universal primer.

For real time PCR, a passive reference dye, ROX™ dye, can be included in PCR reactions to provide an internal reference to which the reporter-dye signal can be normalized during data analysis. Normalization can be accomplished using Applied Biosystems' Sequence Detection System (SDS) software.

In certain embodiments, single-stranded amplification products can be generated by methods including, without limitation, asymmetric PCR, asymmetric reamplification, nuclease digestion, and chemical denaturation. For example, single-stranded sequences can be generated by combining at least one first primer or at least one second primer from a primer set, but not both, in an amplification reaction mixture, or by transcription, for example, when a promoter-primer is used in a first amplification mixture, a second amplification mixture, or both.

Polymerase: The term "polymerase," as used herein, refers to a polypeptide that is able to catalyze the addition of nucleotides or analogs thereof to a nucleic acid in a template dependent manner, for example, the addition of deoxyribonucleotides to the 3'-end of a primer that is annealed to a nucleic acid template during a primer extension reaction. Nucleic acid polymerases can be thermostable or thermally degradable. Suitable thermostable polymerases include, but are not limited to, polymerases isolated from *Therms aquaticus*, *Therms thermophilus*, *Pyrococcus woesei*, *Pyrococcus furiosus*, *Thermococcus litoralis*, and *Thermotoga maritima*. Suitable thermodegradable polymersases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include but are not limited to T7, T3, SP6 RNA polymerases; and AMV, M-MLV and HIV reverse transcriptases.

Commercially available polymerases include, but are not limited to AMBION'S SUPERTAQ®, TAQFS ®, AMPLITAQ® CS (Applied Biosystems), AMPLITAQ® FS (Applied Biosystems), KENTAQ1® (AB Peptide, St. Louis, Mo.), TAQUENASE® (Scien Tech Corp., St. Louis, Mo.), THERMOSEQUENASE® (Amersham), Bst polymerase, READER™Taq DNA polymerase, VENT® DNA polymerase, VENT$_R$® DNA Polymerase, VENT$_R$® (exo⁻) polymerase and DEEPVENT® DNA polymerase, (all VENT® polymerases can be obtained from New England Biolabs), PFUTurbo™ DNA polymerase (Stratagene), Pwo polymerase, Tth DNA polymerase, KlenTaq-1 polymerase, SEQUENASE™ 1.0 DNA polymerase (Amersham Biosciences), SEQUENASE™ 2.0 DNA polymerase (United States Biochemicals), and an enzymatically active mutant and variant thereof.

Descriptions of DNA polymerases can be found in, among other places, Lehninger *Principles of Biochemistry*, 3d ed., Nelson and Cox, Worth Publishing, New York, N.Y., 2000, particularly Chapters 26 and 29; Twyman, *Advanced Molecular Biology: A Concise Reference*, Bios Scientific Publishers, New York, N.Y., 1999; Ausubel et al., *Current Protocols in Molecular Biology*, John Wiley & Sons, Inc., including supplements through May 2005 (hereinafter "Ausubel et al."); Lin and Jaysena, *J. Mol. Biol.* 271:100-11, 1997; Pavlov et al., *Trends in Biotechnol.* 22:253-60, 2004; and *Enzymatic Resource Guide: Polymerases*, 1998, Promega, Madison, Wis.

In various detection embodiments, amplification is optionally followed by additional steps, for example, but not limited to, labeling, sequencing, purification, isolation, hybridization, size resolution, expression, detecting and/or cloning. In certain embodiments, one or both PCR primers can comprise a label, such as, for example, a fluorophore. A label can facilitate detection of an amplification product comprising a labeled PCR primer. In various detection embodiments, following the PCR, biotinylated strands can be captured, separated, and detected.

Multiplex Assays: The term "multiplex assays" refers to PCR reactions that use more than two primers in a single reaction and at the same time so that more than one different amplified product is produced and detected. For example, more than two pair of amplification primers are contacted at the same time and/or in the same solution. Several target RNAs or DNAs can be detected simultaneously using multiplex assays. A multiplex reaction can also include a multiplicity of singleplex PCR reactions run in parallel, e.g., the TAQMAN® Low Density Array (TLDA). Sample preparation processes described herein have been demonstrated to be compatible with multiplex assays.

Real-time PCR: As used herein, "real-time PCR" refers to the detection and quantitation of a DNA, a RNA or a surrogate thereof in a sample. In some embodiments, the amplified segment or "amplicon" can be detected using a 5'-nuclease assay, particularly the TAQMAN® assay as described by e.g., Holland et al. (*Proc. Natl. Acad. Sci. USA* 88:7276-7280, 1991); and Heid et al. (*Genome Research* 6:986-994, 1996). For use herein, a TAQMAN® nucleotide sequence to which a TAQMAN® probe binds can be designed into the primer portion, or known to be present in a RNA or a DNA of a sample.

"$T_m$" refers to the melting temperature (temperature at which 50% of the oligonucleotide is a duplex) of an oligonucleotide determined experimentally or calculated using the nearest-neighbor thermodynamic values of Breslauer et al. (*Proc. Natl. Acad. Sci. USA* 83:3746 3750, 1986) for DNA or Freier et al. (*Proc. Natl. Acad. Sci. USA* 83:9373-9377, 1986) for RNA. In general, the $T_m$ of the TAQMAN® probe is about 10 degrees above the $T_m$ of amplification primer pairs. Amplification primer sequences and double dye-labeled TAQMAN® probe sequences can be designed using PRIMER EXPRESS™ (Version 1.0, Applied Biosystems, Foster City, Calif.) or mFOLD™ software (now UNIFold™) (IDT, San Jose, Calif.).

When a TAQMAN® probe is hybridized to DNA, RNA or a surrogate thereof, the 5'-exonuclease activity of a thermostable DNA-dependent DNA polymerase such as SUPERTAQ® (a Taq polymerase from *Therms aquaticus*, Ambion, Austin, Tex.) digests the hybridized TAQMAN® probe during the elongation cycle, separating the fluor from the quencher. The reporter fluor dye is then free from the quenching effect of the quencher moiety resulting in a decrease in FRET and an increase in emission of fluorescence from the fluorescent reporter dye. One molecule of reporter dye is generated for each new molecule synthesized, and detection of the free reporter dye provides the basis for quantitative interpretation of the data. In real-time PCR, the amount of fluorescent signal is monitored with each cycle of PCR. Once the signal reaches a detectable level, it has reached the "threshold or cycle threshold (Ct)." A fluorogenic PCR signal of a sample can be considered to be above background if its Ct value is at least 1 cycle less than that of a no-template control sample. The term "Ct" represents the PCR cycle number when the signal is first recorded as statistically significant. Thus, the lower the Ct value, the greater the concentration of nucleic acid target. In the TAQMAN® assay, typically each cycle almost doubles the amount of PCR product and therefore, the fluorescent signal should double if there is no inhibition of the reaction and the reaction was nearly 100% efficient with purified nucleic acid. Certain systems such as the ABI 7700 and 7900HT Sequence Detection Systems (Applied Biosystems, Foster City, Calif.) conduct monitoring during each thermal cycle at a pre-determined or user-defined point.

Detection method embodiments using a TAQMAN® probe sequence comprise combining the stopped mixture or the reverse transcribed mixture with PCR reagents, including a primer set having a forward primer and a reverse primer, a DNA polymerase, and a fluorescent detector oligonucleotide TAQMAN® probe, as well as dNTP's and a salt, to form an amplification reaction mixture; subjecting the amplification reaction mixture to successive cycles of amplification to generate a fluorescent signal from the detector probe; and quantitating the nucleic acid presence based on the fluorescent signal cycle threshold of the amplification reaction.

Protocols and reagents for means of carrying out further 5'-nuclease assays are well known to one of skill in the art, and are described in various sources. For example, 5'-nuclease reactions and probes are described in U.S. Pat. No. 6,214,979 issued Apr. 10, 2001; U.S. Pat. No. 5,804,375 issued Sep. 8, 1998; 5,487,972 issued Jan. 30, 1996; and U.S. Pat. No. 5,210,015 issued May 11, 1993, all to Gelfand et al.

In various embodiments, a detection method can utilize any probe that can detect a nucleic acid sequence. In some configurations, a detection probe can be, for example, a TAQMAN® probe described supra, a stem-loop molecular beacon, a stemless or linear beacon, a PNA MOLECULAR BEACON™, a linear PNA beacon, non-FRET probes, SUNRISE®/AMPLIFLUOR® probes, stem-loop and duplex SCORPION™ probes, bulge loop probes, pseudo knot probes, cyclicons, MGB ECLIPSE™ probe, a probe complementary to a ZIPCODE™ sequence, hairpin probes, peptide nucleic acid (PNA) light-up probes, self-assembled nanoparticle probes, and ferrocene-modified probes as known by one of ordinary skill in the art. A detection probe having a sequence complementary to a detection probe hybridization sequence, such as a ZIPCODE™ sequence, a fluorphore and a mobility modifier can be, for example, a ZIPCHUTE™ probe supplied commercially by Applied Biosystems (Foster City, Calif.).

Label or Reporter: A "label" or "reporter," as used herein, refers to a moiety or property that allows the detection of that with which it is associated and, for use herein, has emission spectra at between and including 300 nm to 750 nm. In certain embodiments, the emission spectra is at less than about 499 nm such as for blue emitters such as certain Alexa Fluor emitters, Cascade Blue, and Pacific Blue; at 500 nm to 549 nm emitters such as for green emitters such as certain Alexa Fluor emitters, BODIPY FL, fluorescein (FITC), CYANINE™ 2 dye, Catskill Green, 5-FAM™ dye, 6-FAM™ dye, succinimidyl ester, JOE™ dye, MFP488, the Oregon Green emitters and TET™ dye; at 550 nm to 584 nm emitters such as yellow emitters such as certain Alexa Fluor emitters, CYANINE™ 3 dye, HEX™ dye, NED™ dye, R-Phycoerythrin (R-PE), 5-TAMRA™ dye, TRITC (Rhodamine), and VIC® dye; at 585 nm to 615 nm emitters such as orange emitters such as certain Alexa Fluor emitters, CYANINE™ 3.5 dye, Lissamine Rhodamine, ROX™ dye, and R-Phycoerythrin-TEXAS RED® dye; and at 616 nm to 700 nm emitters such as red emitters such as certain Alexa Fluor emitters, CYANINE™ 5 dye, Quantum Red, Rodamine Red-X, and TEXAS RED® dye.

The label can be attached covalently or non-covalently to a DNA product, to a RNA product, or to a surrogate thereof such as an amplicon thereof. Commonly used labels include dyes that are negatively charged, such as dyes of the fluorescein family including, e.g. FAM™ dye, HEX™ dye, TET™ dye, JOE™ dye, NAN and ZOE; or dyes that are neutral in charge, such as dyes of the rhodamine family including, e.g., TEXAS RED® dye, ROX™ dye, R110, R6G, and TAMRA™ dye; or dyes that are positively charged, such as dyes of the CYANINE™ family including e.g., Cy™2 dye, Cy™3 dye, Cy™5 dye, Cy™5.5 dye and Cy™7 dye. FAM™ dye, HEX™ dye, TET™ dye, JOE™ dye, NAN, ZOE, ROX™ dye, R110, R6G, and TAMRA™ dyes are available from, e.g., Applied Biosystems (Foster City, Calif.) or Perkin-Elmer, Inc. (Wellesley, Mass.); TEXAS RED® dye is available from, e.g., Molecular Probes, Inc. (Eugene, Oreg.); and Cy™2 dye, Cy™3 dye, Cy™5 dye, Cy™5.5 dye and Cy™7 dye, and are available from, e.g., Amersham Biosciences Corp. (Piscataway, N.J.). In certain amplification embodiments, the fluorescer molecule is a fluorescein dye and the quencher molecule is a rhodamine dye.

A label or reporter can comprise both a fluorophore and a fluorescence quencher. The fluorescence quencher can be a fluorescent fluorescence quencher, such as the fluorophore TAMRA™ dye, or a non-fluorescent fluorescence quencher (NFQ), for example, a combined NFQ-minor groove binder (MGB) such as an MGB ECLIPSE™ minor groove binder supplied by Epoch Biosciences (Bothell, Wash.) and used with TAQMAN™ probes (Applied Biosystems, Foster City, Calif.). The fluorophore can be any fluorophore that can be attached to a nucleic acid, such as, for example, FAM™ dye, HEX™ dye, TET™ dye, JOE™ dye, NAN, ZOE, TEXAS RED® dye, ROX™ dye, R110, R6G, TAMRA™ dye, Cy™2 dye, Cy™3 dye, Cy™5 dye, Cy™5.5 dye and Cy™7 dye as cited above as well as VIC® dye, NED™ dye, LIZ® dye, ALEXA, Cy™9 dye, and dR6G.

Further examples of labels include black hole quenchers (BHQ) (Biosearch), Iowa Black (IDT), QSY quencher (Molecular Probes), and Dabsyl and Dabcel sulfonate/carboxylate Quenchers (Epoch).

Labels can also comprise sulfonate derivatives of fluorescein dyes, phosphoramidite forms of fluorescein, phosphoramidite forms of CY™5 dye (available for example from Amersham), and intercalating labels such as ethidium bromide, SYBR™ Green I dye and PICOGREEN™ dye (Molecular Probes). Generally, an intercalating label is a molecule that reversibly inserts between two other molecules (or groups) such as between the bases of DNA.

In various embodiments, qPCR reactions can include master mixes such as the TAQMAN® Gene Expression Master Mix, TAQMAN® Universal PCR Master Mix, TAQMAN® Fast Universal PCR Master Mix, Power SYBR® Green PCR Master Mix, Fast SYBR® Green Master Mix, TAQMAN® RNA-to-$C_T$™ 1-Step Kit, and the Power SYBR® Green RNA-to-$C_T$™ 1-Step Kit, for example, all from Applied Biosystems.

In various embodiments, detection of emission such as fluorescence can be by any method known to skilled artisans, and can include, for example, real time detection for PCR or end point detection. Detection of fluorescence, for example, can be qualitative or quantitative. Quantitative results can be obtained, for example, with the aid of a fluorimeter, for example a fluorimeter as part of an integrated nucleic acid analysis system, such as, for example, an Applied Biosystems ABI PRISM™ 7900HT Sequence Detection System. Furthermore, quantitative results can be obtained in some configurations using a real-time PCR analysis. Some non-limiting examples of protocols for conducting fluorogenic assays such as TAQMAN® assays, including analytical methods for performing quantitative assays, can be found in publications such as, for example, "SNPLEX™ Genotyping System 48-plex", Applied Biosystems, 2004; "User Bulletin #2 ABI PRISM™ 7700 Sequence Detection System," Applied Biosystems 2001; "User Bulletin #5 ABI PRISM™ 7700 Sequence Detection System," Applied Biosystems, 2001; and "Essentials of Real Time PCR," Applied Biosystems (Foster City, Calif.). Fluorogenic PCR assays used in some configurations of the present teachings can be performed using an automated system, such as, for example, an ABI 7700 Sequence Detection System (Applied Biosystems).

In some embodiments, detection can be achieved using microarrays or bead arrays and related software, such as the Applied Biosystems Array System with the Applied Biosystems 1700 Chemiluminescent Microarray Analyzer, and other commercially available array systems available from Affymetrix, Agilent, and Illumina, among others (see also Gerry et al., *J. Mol. Biol.* 292:251-62, 1999; De Bellis et al., *Minerva Biotec* 14:247-52, 2002; and Stears et al., *Nat. Med.* 9:140-45, including supplements, 2003).

Further method embodiments for detection of DNA, RNA, or a surrogate thereof comprise use of a promoter sequence or a complement thereof and the method includes combining the DNA, RNA, or a surrogate thereof with PCR reagents, including at least one primer set and a DNA polymerase, to form a first amplification reaction mixture subjecting the first amplification reaction mixture to at least one cycle of amplification to generate a first amplification product comprising the promoter sequence; combining the first amplification product with an RNA polymerase and a ribonucleoside triphosphate solution comprising at least one of rATP, rCTP, rGTP, rUTP, or aminoallyl-rUTP to form a transcription reaction mixture; incubating the transcription reaction mixture under appropriate conditions to generate an RNA transcription product; and detecting presence of the target nucleic acid by detection of the RNA transcription product or a portion thereof. In certain embodiments, the polymerase is reverse transcriptase.

Exemplary RNA polymerases include T7, T3, or SP6 RNA polymerase and exemplary promoters include the T7, T3, or SP6 promoters. The RNA transcription product or a portion thereof can be detected using, for example, the aminoallyl-rUTP which is available for coupling to a succinimide ester label for detection.

Enzymatically Active Mutants or Variants Thereof: The term "enzymatically active mutants or variants thereof" when used in reference herein to an enzyme such as a protease, deoxyribonuclease, a polymerase or the like, refers to a polypeptide derived from the corresponding enzyme that retains at least some of the desired enzymatic activity. Enzymatically active mutants or variants include, for example, fragments, recombinantly expressed fragments, naturally-occurring mutants, mutants generated using mutagens, genetically engineered mutants, mutants due to amino acid insertions or deletions or due to nucleic acid nonsense, missense, or frameshift mutations, reversibly modified enzymes, splice variants, polypeptides having modifications such as altered glycosylation, disulfide bonds, hydroxyl side chains, and phosphate side chains, or crosslinking, and the like. Protocols for measuring enzymatic activity using an appropriate assay are known to one of ordinary skill in the art.

Cell lysates provided herein are useful for any method of detection of nucleic acid that uses a dye that has a detectable emission. In particular, a dye or label that fluoresces in the 500 nm to 615 nm range such as used in PCR, RT-PCR, qRT-PCR, siRNA-mediated gene knockdown, high-throughput assessment of any kind particularly in 96-well or 384-well plates is envisioned for use herein. Samples can be processed directly in culture plates, minimizing sample handling and the potential for sample loss or transfer error. The cell lysis protocol in 384-well plates is readily automated on robotic platforms. cDNA can then be synthesized directly from the lysate using the High Capacity cDNA RT Kit, or the High Capacity RNA-to-cDNA kit, and real-time PCR performed using the TAQMAN® Gene Expression Master Mix (Applied Biosystems, Foster City, Calif.) on the 7900HT Real Time PCR System. Custom libraries of Silencer® Pre-designed siRNAs and TAQMAN® Gene Expression Assays plated to specification in 384-well plates can be obtained directly from the manufacturer (Applied Biosystems). Processes provided by the teachings herein ensure high-throughput processing, efficient use of reagents and instruments, a minimal amount of hands-on time, and accurate and reliable results.

Kits: A "kit," as used herein, refers to a combination of items for performing a sample preparation process as set forth herein. Embodiments of kits comprise, for example, lysis mixture components and stop mixture components. Lysis mixture components comprise a polypeptide having protease activity, a surfactant comprising TRITON X-114™, THESIT™, TRITON X-100™, NONIDET P-40™, or a combination thereof, and a polypeptide having deoxyribonuclease activity. The lysis mixture components are substantially free of a cation chelator. Stop mixture components comprise a cation chelator, and an inhibitor of the polypeptide having protease activity. Components of kits may be packaged together or separately as desired for the processes described herein.

Kit embodiments can further comprise reagents for reverse transcription, such as reverse transcriptase, a reverse primer, dNTPs or a reverse transcriptase buffer, or can further comprise reagents for PCR, such as a DNA polymerase, for example.

Embodiments of kits can further comprise a detector probe such as a 5'-nuclease probe such as a TAQMAN® probe, an RNA or a DNA control nucleic acid, reagents for sample collection, an RNA polymerase or an enzymatically active mutant or variant thereof, or ribonucleotides rATP, rCTP, rGTP, rUTP, or aminoallyl-rUTP. In certain kit embodiments, amplification primers can be attached to a solid support such as a microarray.

In some kit embodiments, an enzyme comprising reverse transcriptase activity and thermostable DNA-dependent DNA polymerase activity are the same enzyme, e.g., *Thermus* sp. ZO5 polymerase or *Thermus thermophilus* polymerase.

When components of a kit are provided in one and/or more liquid solutions, the liquid solution comprises an aqueous solution that can be a sterile aqueous solution. In some embodiments, at least one component of the kit can be provided as a dried powder. When reagents and/or components are provided as a dry powder, the powder can be reconstituted by the addition of a suitable solvent. It is envisioned that the solvent can also be provided in another container means. The container means will generally include at least one vial, test tube, flask, bottle, syringe and/or other container means, into which the solutions are placed, and in some embodiments, suitably aliquoted. The kits can also comprise a further container means for containing a sterile, pharmaceutically acceptable buffer and/or other diluent.

A kit can also include instructions for employing the kit components as well the use of any other reagent not included in the kit. Instructions can include variations that can be implemented.

Aspects of the present teachings can be further understood in light of the following examples, which should not be construed as limiting the scope of the present teachings in any way.

EXAMPLE 1

Effect of EDTA on Preparation of Samples for Nucleic Acid Analysis

Studies were conducted on the effect of EDTA on DNase I and proteinase K activity for preparation of samples for nucleic acid analysis. DNase I (0.2 U) was mixed with 10 uL DNaseALERT™ solution (catalog no. AM1970, AMBION® Inc., Austin Tex.) in Buffer A (10 mM Tris pH 7.5, 3 mM $MgCl_2$, 1 mM $CaCl_2$) with 1 mM EDTA (FIG. 2, ♦, diamonds), Buffer A without EDTA (FIG. 2, ●, circles), or DNase I buffer (FIG. 2, ■, squares, 10 mM Tris pH 7.5, 2.5 mM $MgCl_2$, 0.5 mM $CaCl_2$) in a final volume of 100 ul. The 590 nm fluorescence intensity with 544 nm excitation was measured with time.

FIG. 2 provides data demonstrating that 1 mM EDTA appears to have an inhibitory effect on DNase I activity using the DNaseALERT™ system assay. In addition, the DNase I buffer having less $Mg^{++}$ and less $Ca^{++}$ provided slightly better results than Buffer A.

In a separate study, proteinase K activity was shown to be independent of EDTA concentration.

EXAMPLE 2

Effect of Surfactant on Preparation of Samples for Nucleic Acid Analysis

Lysis efficacies of seven surfactants were tested by PI staining (DNA fluorochrome propidium iodide stain for viability, 1 mg/ml) of $10^5$ HeLa cells treated with 0.01% to 5% surfactant. The buffer was 10 mM Tris pH 7.5, 2.5 mM $MgCl_2$, 0.5 mM $CaCl_2$.

TWEEN™ 20, TWEEN™ 40, and TWEEN™ 80 were not effective at lysing cells at concentrations up to 3%. NONIDET™ P-40 (Roche, Mannheim, Germany) was effective for lysis at concentrations at and above 0.1% to 5%. THESIT™ was effective for lysis at concentrations at and above 0.05% to 5%. TRITON™ X-114 (Dow Chemical) was effective for lysis at concentrations at and above 0.1% to 3%. TRITON™ X-100 (Dow Chemical) was shown to be effective for lysis at concentrations at and above 0.05%; a 1% solution was considered as a control for full lysis. Results using TRITON™ X-114 surfactant at six different concentrations and using TRITON X-100™ surfactant at one concentration as determined by propidium iodide (PI) staining (1 mg/ml) of $10^5$ HeLa cells are provided in FIG. 3.

The effects of surfactants on PCR reactions were then studied. qPCR (20 uL) reactions with 4 ng Human Universal reference liver cDNA (Catalog No. 780622; STRATAGENE®, La Jolla, Calif.) were performed by adding 2uL of surfactant resuspended in 10 mM Tris pH 7.5 at concentrations of 0.0%, 0.01%, 0.03%, 0.1%, 0.3%, and 1%. qPCR reactions were carried out using the TAQMAN® Universal PCR Master Mix (Applied Biosystems Catalog No. 4304437), and qRT-PCR reactions were carried out using the TAQMAN® One-Step RT-PCR Master Mix (Applied Biosystems Catalog No. 4309169). TAQMAN® gene expression assays were used to determine expressions levels of genes PPIA (peptidylprolyl isomerase A (cyclophilin A)) and B2M (β-2-microglobulin).

THESIT™, TRITON X-100™ and NONIDET P-40™ had negative effects on PCR as demonstrated by an increase in Ct at concentrations at or above 0.3% (0.03% final in PCR) as shown by the data of FIG. 4 (THESIT™, diamonds, dashed line; TRITON X-100™, squares, dotted line; and NONIDET P-40™, circles, solid line). TRITON X114™ had no effect on qPCR, even at 1% (0.1% final in PCR) as shown by the data of FIG. 4 (triangles, solid line). This effect was seen with TAQMAN® Universal PCR Master Mix (Applied Biosystems Catalog No. 4304437) that uses AMPLITAQ GOLD® DNA polymerase. These results may be due to an increase in cloudiness of the solution and/or an increase in FAM™ background fluorescence (Ro) as shown by the data of FIG. 5 (TRITON X-114™ (triangles, solid line), THESIT™ (diamonds, dashed line), TRITON X-100™ (squares, dotted line), and NONIDET P-40™ (circles, solid line)). ROX™ background fluorescence was not affected.

Each of FIG. 6A-FIG. 6D provides an amplification plot of Rn (fluorescence corrected to a reference dye, ROX™) vs cycle number in the presence of one of four surfactants and at concentrations cited for data of FIG. 4 and FIG. 5. The fluor used in the PCR reaction was FAM™ and the quencher was MGB™. THESIT™ (data of FIG. 6A) increased Ro (background fluorescence) but had little effect on Rn. TRITON X-100™ (data of FIG. 6B) and NONIDET P-40™ (data of FIG. 6D) increased background fluorescence and decreased Rn. TRITON X-114™ (data of FIG. 6C) slightly increased background fluorescence and had little to no effect on Rn at lower concentrations. For use with FAM™ dye detection, TRITON X-114™ appears to be an exemplary surfactant for use in the lysis buffer.

In separate studies, the surfactants cited above were found to be compatible with DNase I and proteinase K activity.

EXAMPLE 3

Inactivation of Lysis Enzymes for Preparation of Samples for Nucleic Acid Analysis Some embodiments herein provide for chemical inhibition of proteinase K and of DNase I so as to provide the isothermal characteristics of certain preparation methods herein. In some embodiments, such chemical inhibition is also designed to be compatible with RT-PCR.

PMSF (phenylmethylsulfonylfluoride), AAPV (methoxysuccinyl-Ala-Ala-Pro-Val-chloromethyl ketone, SEQ ID NO:1), TLCK (N-tosyl-L-lysine-chloromethyl ketone), leupeptin (Ac-Leu-Leu-Arg-CHO), AEBSF, N-Acetyl-eglin C (Catalog No. E7888; Sigma-Aldrich, St. Louis Mo.), aprotinin (also known as bovine pancreatic trypsin inhibitor, BPTI), benzamidine, BSA (bovine serum albumin), antipain dihydrochloride, and AAPA (methoxysuccinyl-Ala-Ala-Pro-Ala-chloromethyl ketone, SEQ ID NO:3) were studied for inhibition of proteinase K (PK) at room temperature and for compatibility with RT-PCR. PK (600 ug/ml) was mixed with increasing amounts of test inhibitor and allowed to react for 3 min at room temperature. RNase A was added and the mixture was incubated for 10 min. The RNase A was mixed with RNaseALERT™ substrate (AMBION®, Catalog No. AM1964) and incubated for 10 min. The fluorescence of the RNaseALERT™ substrate was measured at 520 nm. PMSF, AAPV (SEQ ID NO:1), leupeptin, aprotinin, BSA, and antipain were found to be capable of inhibiting PK at room temperature. Under the conditions employed, TLCK, AEBSF, N-acetyl-Eglin C, benzamidine, and AAPA (SEQ ID NO:3) did not show inhibition of PK. The AAPA (SEQ ID NO:3) preparation obtained from the supplier appears to have been inferior since AAPA (SEQ ID NO:3) is expected to be inhibitory for PK.

Compatibility with RT-PCR was studied by combining each inhibitor with a lysis solution (100 mM Tris pH 7.5, 25 mM $MgCl_2$, 5 mM $CaCl_2$, 0.1% TRITON X114™, 100 U/ml DNase, 600 ug/ml PK) and purified HeLa RNA (1.8 ug). The samples were reverse transcribed using a Reverse Transcriptase Kit (Applied Biosystems Catalog No. 4368813) and the resulting cDNA was subjected to real time PCR with the TAQMAN® Universal PCR Master Mix (Applied Biosystems Catalog No. 4304437).

Minimal RT-PCR inhibition was seen with AAPV (SEQ ID NO:1) and PMSF, each at concentrations up to 2 mM in the stopped mixture (e.g., up to 400 uM in an RT reaction). Aprotinin was inhibitory at all concentrations tested. In a similar study, these 3 inhibitors were tested in 1-step RT-PCR and only AAPV (SEQ ID NO:1) was compatible. Both PMSF and aprotinin showed RT-PCR inhibition for the one-step reaction.

These data demonstrate that AAPV (SEQ ID NO:1) and PMSF are effective inhibitors of proteinase K. In some embodiments, the concentration of PMSF is kept below about 2 mM in the stopped mixture. For one-step RT-PCR, AAPV (SEQ ID NO:1) is effective. To determine the concentration of AAPV (SEQ ID NO:1) for inhibition of proteinase K in the lysis solution, 50 uL lysis solution was mixed with 5 uL of stop solution with varying amounts of AAPV (SEQ ID NO:1) (11 mM Tris, 44 mM EGTA, 0.5-1 mM AAPV (SEQ ID NO:1)) and incubated for 10 min. RNase A (15 ug) was added to each sample and the samples were held for 10 min at room temperature. The reaction mixture was heated for 30 min at 95° C. and analyzed using a Protein 50 Bioanalyzer chip (2100 Bioanalyzer, Agilent, Santa Clara, Calif.). The Bioanalyzer protein gel data are provided by FIG. 7 in which the lower marker is at about 3.5 kDa; the next higher prominent bands are system peaks at about 4.0-4.5 kDa; intact RNase A is at about 20 kDa; and proteinase K is at about 35 kDa. Lanes are labeled as follows: (L) Ladder, (1) RNase Only, (2) PK Only, (3)-(8) AAPV (SEQ ID NO:1) at 1 mM (3), 0.75 mM (4), 0.5 mM (5), 0.25 mM (6), 0.125 mM (7), and 0 mM (8). AAPV (SEQ ID NO:1) was capable of inhibiting PK (100 ug/ml) at concentrations as low as 0.25 mM (lane 6) and at even lower concentrations when incubated with PK for a longer period of time prior to addition of the RNase A substrate.

The ability of EGTA to inhibit DNase I activity and the limiting amount of EGTA that could be used in RT-PCR was determined. EGTA (88 mM; final conc. of 8 mM) was added to the stop solution for DNase I inactivation. The pH of the stop solution was 8.0 for AAPV (SEQ ID NO:1) inactivation of proteinase K. Tris-base with HCl as needed for pH adjustment (11 mM; final conc of 1 mM) was used for buffering the solution. EGTA was found to inhibit DNase I at 4 mM or higher.

EXAMPLE 4

Isothermal Sample Preparation Embodiments

Exemplary non-limiting embodiments of lysis solutions are prepared by obtaining stock solutions of 1M Tris-base pH 8.0, 1M $MgCl_2$, 1M $CaCl_2$, 1M DTT, proteinase K at 20 mg/ml, 20% TRITON X-114™ surfactant and nuclease-free water. Stock solutions are diluted to form a lysis solution of Tris pH 8.0, 10 mM; $MgCl_2$, 0.5 mM; $CaCl_2$, 0.5 mM; a reducing agent such as DTT, β-mercaptoethanol or dithioerythritol, 0.01 mM; protease such as proteinase K, 100 ug/ml; and TRITON X114™ surfactant, 0.1%, in nuclease free water. The pH is adjusted to pH 7.8 +/−0.1 with HCl at a temperature of 19° C-25° C. (a range of pH values is about 7.5 to 8.2). The lysis solution can be stored at −20° C., at 4° C., and has been found to be stable at 25° C. for one year.

A lysis mixture (termed lysis buffer in FIG. 1A) is prepared by combining the lysis solution with a deoxyribonuclease such as DNase I at a concentration of 300 U/ml (a range of 100 U/ml-600 U/ml can be used) for those embodiments in which it is desired to remove DNA. In certain embodiments, the volume of deoxyribonuclease added is less than about 1% of the volume of the final lysis reaction. Lysis can be carried out in a 50 uL volume at a pH of 7.8.

Exemplary embodiments of a stop mixture include a protease inhibitor having inhibitory activity for the protease of the lysis mixture; and a divalent cation chelator that, by chelating divalent cations of the lysis mixture, provides for inactivation of the deoxyribonuclease of the lysis mixture. Therefore a lysis mixture and a stop mixture are tailored to work together.

Stock solutions for an exemplary stop mixture include a protease inhibitor such as AAPV (SEQ ID NO:1) in DMSO (100 mM), 1M Tris-base pH 8.3, a cation chelator such as 200 mM EGTA, a reducing agent such as 1M DTT and nuclease free water. An exemplary stop mixture for use with proteinase K and DNase I includes AAPV (SEQ ID NO:1), 11 mM; 1 M Tris pH 8.3, 11 mM; 200 mM EGTA, 88 mM; RNase Inhibitor such as RIP, 2.2 U/ul; and 1M DTT, 0.11 mM in nuclease free water. The pH is adjusted to 8.0 +/−0.1 (at 19° C.-25° C). with HCl or KOH as needed. For this exemplary embodiment, 5 uL of stop solution is added to 50 uL of lysis mixture to form a stopped mixture.

Certain embodiments of the processes for preparing a sample for nucleic acid analysis are carried out as follows. DNase I is mixed with lysis solution and the resultant lysis mixture is stored on ice. For 1-$10^6$ cultured mammalian cells, cells are pelleted (~800×g for 5 min), the media is removed and the cells are washed with 50 uL of 1× PBS and re-pelleted. The supernatant is removed. Adhered cells in 96- or 384-well plates (1 to $10^6$ cells) can also be used with this procedure. No centrifugation is required since the cells remain adhered to the plate throughout the washing procedure.

Lysis mixture (50 ul) is added to the pellet and the pellet is resuspended by pipetting. The lysis reaction is incubated for 5 minutes at room temperature (19° C.-25° C.) or for about 8 minutes for miRNA sample preparation embodiments, also at room temperature. Stop solution (5 ul) is added directly into each lysis reaction, mixed 5× by pipetting, and incubated for 2 minutes at room temperature (19° C.-25° C.). The stopped lysate is ready for downstream nucleic acid analysis, detection and/or amplification and is used within about 20 minutes for such a downstream procedure or is frozen for later use.

A 5-minute lysis time, a 2-minute stop time, and mixing 5× with a pipette are provided for some embodiments of nucleic acid preparation methods of the present teachings. An 8-minute lysis time, a 2-minute stop time, and mixing 5× with a pipette are provided for embodiments of miRNA nucleic acid preparation methods of the present teachings. Temperatures between 16° C. and 28° C. are provided for certain embodiments of isothermal preparation methods. Washing with 50 uL PBS or media (without fetal bovine serum) is acceptable prior to lysis.

Nucleic acid analysis, detection and/or amplification can include a reverse transcription step, a real-time PCR reaction, and/or an RNA transcription step comprising use of an RNA polymerase. The sample preparation process provided by teachings herein provides components that minimally interfere with enzymatic activity and detection methods.

The data of FIG. 8 demonstrate the linearity and efficiency of certain sample preparation processes as provided herein using the TAQMAN® Gene Expression assay for β-actin (Applied Biosystems) over 4 logs of cellular input from 10 cells up to 100,000 cells per lysis reaction. The data demonstrate good linearity down to an input of as few as 10 cells.

Sample preparation processes as provided by teachings herein are compatible with a large number of cell lines. Table 1 provides a listing of cells lines that have been tested.

TABLE 1

Cell Lines tested using Preparation Processes of Embodiments Herein

| Cell Line | Growth | Source Species | Source Tissue |
|---|---|---|---|
| HeLa | adherent | H. sapiens | Cervical Adenocarcinoma |
| HepG2 | adherent | H. sapiens | Liver Carcinoma |
| Primary Hepatocytes | adherent | H. sapiens | Liver |
| SK-N-AS | adherent | H. sapiens | Brain Neuroblast |
| SK-N-SH | adherent | H. sapiens | Brain Neuroblast |
| U-87 MG | adherent | H. sapiens | Brain Glioblastoma |
| ME-180 | adherent | H. sapiens | Cervical Epidermoid Carcinoma |
| A549 | adherent | H. sapiens | Lung Carcinoma |
| Jurkat | suspension | H. sapiens | Acute T-Cell Leukemia |
| PC-12 | loosely adherent | R. norvegicus (rat) | Adrenal Pheochromocytoma |
| PT-K75 | adherent | S. scrofa (pig) | Nasal Turbinate Mucosa |
| NIH/3T3 | adherent | M. musculus (mouse) | Embryonic Fibroblast |
| Raji | suspension | H. sapiens | B Lymphocyte |
| HEK-293 | adherent | H. sapiens | Kidney |
| COS-7 | adherent | C. aethiops (monkey) | Kidney |
| CHO-K1 | adherent | C. griseus (hamster) | Ovary |
| NCI-H460 | adherent | H. sapiens | Lung Carcinoma |
| DU 145 | adherent | H. sapiens | Prostate Carcinoma |
| K562 | suspension | H. sapiens | Bone Marrow Leukemia |
| U-2 OS | adherent | H. sapiens | Osteosarcoma |
| Huh-7 | adherent | H. sapiens | Liver Carcinoma |
| Neuro 2A | adherent | M. musculus (mouse) | Brain blastoma |
| BJ | adherent | H. sapiens | Foreskin Fibroblast |

In addition, $C_T$ values obtained using lysates as prepared using processes provided herein were found to be essentially equivalent to $C_T$ values obtained with purified RNA. Stopped lysates and purified RNA from 5000 HeLa cells were prepared in parallel and evaluated with 78 TAQMAN® Gene Expression Assays on an Applied Biosystems 7900HT Real-Time PCR Instrument. The $C_T$ value obtained from the stopped lysates is plotted against the $C_T$ value for the same assay using purified RNA as shown in FIG. 9A. The linear correlation coefficient is Y(stopped lysates)=0.951X(Pure RNA)+1.05, $R^2$=0.933.

The assays of FIG. 9A were expanded to provide data for 40,000 cultured cells (a mixture of 5 cell lines) and evaluated with 151 TAQMAN® Gene Expression Assays on an Applied Biosystems 7500 Fast Real-Time PCR Instrument. The $C_T$ value obtained from the stopped lysates is plotted against the $C_T$ value for the same assay using purified RNA as shown in FIG. 9B. The linear correlation coefficient is Y(stopped lysates)=0.972X(Pure RNA)+0.870, $R^2$=0.973. These data demonstrate comparable performance using the preparation methods herein as compared to purified RNA.

Sample preparation processes of embodiments herein use fewer sample handling and transfer steps as compared to traditional RNA purification strategies. As a result, there is less potential for sample loss and variability among replicates using the isothermal processes herein over traditional RNA purification strategies. That some of the sample preparation processes provided herein are less variable than traditional RNA purification strategies is demonstrated by the following study. HeLa cells (5000) were either subjected to traditional RNA purification or cell lysis using isothermal preparation methods of teachings herein. Twenty-four replicates for each preparation protocol were carried out. Samples were then evaluated using a TAQMAN® Gene Expression Assay for β-actin. Data of FIG. 10 demonstrates a greater sensitivity and reproducibility of replicate stopped lysates compared to purified RNA.

Sample preparation processes of embodiments herein are provided for microRNA quantitation and profiling without RNA isolation. Cells (up to $10^5$-$10^6$) are washed in phosphate-buffered saline and lysed for 8 minutes at room temperature. DNase treatment can be performed concurrently. Lysis is terminated at room temperature for two minutes with stop solution as described above. All of the small RNA species present in a cell are available for analysis since the samples are processed directly. The present sample preparation embodiments have been demonstrated to provide performance equivalent to purified RNA when tested against a panel of 111 TAQMAN® MicroRNA Assays.

Sample preparation processes of embodiments herein also provide the ability to distinguish between highly homologous mature miRNA targets for accurate miRNA expression analysis. For example, the ability of TAQMAN® MicroRNA Assays to distinguish between the highly homologous let-7 family of miRNAs was not affected by the use of sample preparation processes described herein.

Sample preparation processes of embodiments herein also provide methods for analyzing effects of siRNAs for RNA interference activity. For example, duplicate sets of 4000 cells were transfected with 20 different siRNAs and the sets were either lysed using sample preparation processes of embodiments described herein or using the MAGMAX™ RNA purification protocol (Applied Biosystems). The percent remaining expression of target mRNAs was determined for each set and was found to be essentially equivalent. Therefore, the sample preparation embodiments provided herein provide expression data for RNA interference that is essentially equivalent to that of data obtained from purification of the RNA.

Sample preparation processes of embodiments herein also provide methods for single nucleotide polymorphism (SNP) detection. Lysates were generated as described herein from 10,000 HeLa cells, HepG2 cells, Jurkat cells, DU-145 cells, HEK-293 cells, K562 and MCF-7 cells in 50 µl of lysis solution and compared separately to purified DNA from the same cell sources. The TAQMAN® Genotyping Master Mix (Applied Biosystems) was mixed with the SNP assay and 1 ng of DNA (0.5 µl) or 0.5 µl of lysates (~83 cells) was added. PCR was carried out for 40 cycles. FIG. 11 provides data for detection of a SNP obtained from the two methods. "A" contains the genomic DNA and lysates from the HepG2, 293, Jurkat and K562 cell lines. "B" contains the genomic DNA and lysates from HeLa cells. "C" contains the genomic DNA and lysates from MCF-7 and DU-145 cell lines. The data are clustered for allele Y at "A," for allele X at "C" and for cells containing both alleles at "B" thereby showing consistency of results from the two methods. The "D" data provide the no template control samples. Therefore, sample preparation processes of embodiments herein are equivalent in efficacy for determination of SNP detection.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications can be made without departing from the teachings herein. The foregoing examples are provided to better illustrate the present teachings and are not intended to limit the scope of the teachings herein. Certain aspects of the present teachings can be further understood in light of the following claims.

What is claimed is:

1. A process for preparing a sample containing nucleic acid for in situ analysis of nucleic acid or a surrogate thereof, the process comprising:
   contacting the sample containing nucleic acid with a lysis mixture under conditions and for a time to produce a lysate,
   admixing the lysate with a stop mixture at substantially the same temperature as the contacting step to form a stopped mixture compatible with nucleic acid polymerase reaction conditions, and
   contacting the stopped mixture with reagents for nucleic acid polymerization to form a first amplification reaction.

2. The process of claim 1 wherein the sample contains RNA and the nucleic acid polymerase is a reverse transcriptase.

3. The process of claim 1 wherein the sample contains DNA and the nucleic acid polymerase is a DNA polymerase.

4. The process of claim 1 wherein contacting the sample with a lysis mixture is for a time of 2 minutes to 30 minutes.

5. The process of claim 1 wherein the sample comprises one cell to $10^5$ or $10^6$ cells.

6. The process of claim 1 wherein the sample is a fixed sample.

7. The process of claim 1 wherein the sample is obtained by laser capture microdissection.

8. The process of claim 1 wherein the temperature is from 15° C. to 30° C.

9. A process for preparing a sample containing nucleic acid for in situ analysis of nucleic acid or a surrogate thereof, the process comprising:
   contacting the sample containing nucleic acid with a lysis mixture under conditions and for a time to produce a lysate wherein the lysis mixture comprises a polypeptide having protease activity, and a surfactant,
   admixing the lysate with a stop mixture at substantially the same temperature as the contacting step to form a stopped mixture wherein the stop mixture comprises an inhibitor of the polypeptide, and
   contacting the stopped mixture with reagents for nucleic acid polymerization to form a first amplification reaction.

10. The process of claim 9 wherein the sample contains RNA and a reagent for nucleic acid polymerization is a reverse transcriptase.

11. The process of claim 9 wherein the sample contains DNA and a reagent for nucleic acid polymerization is a DNA polymerase.

12. The process of claim 9 wherein contacting the sample with a lysis mixture is for a time of 2 minutes to 30 minutes.

13. The process of claim 9 wherein the sample comprises one cell to $10^5$ or $10^6$ cells.

14. The process of claim 9 wherein the sample is a fixed sample.

15. The process of claim 9 wherein the sample is obtained by laser capture microdissection.

16. The process of claim 9 wherein the temperature is from 15° C. to 30° C.

17. The process of claim 9 further comprising contacting the first amplification reaction with reagents for polymerase chain reaction to generate an amplified product.

18. A process for preparing a sample containing RNA for in situ analysis of RNA or a surrogate thereof, the process comprising:
   contacting the sample containing RNA with a lysis mixture under conditions and for a time to produce a lysate
   wherein the lysis mixture comprises a polypeptide having deoxyribonuclease activity and a surfactant that substantially lacks fluorescence between 300 nm and 750 nm when in use for in situ analysis of RNA or a surrogate thereof, and
   wherein the lysis mixture is substantially free of a cation chelator, wherein the cation chelator is EDTA.

19. The process of claim 18 wherein the lysis mixture further comprises a ribonuclease inhibitor.

20. The process of claim 18 further comprising contacting the lysate, or a portion thereof, with reagents for reverse transcription for a time and under conditions to form cDNA.

21. The process of claim 20 further comprising contacting the cDNA with reagents for PCR.

22. The process of claim 18 wherein the conditions comprise a temperature of 15° C. to 40° C.

23. The process of claim 18 wherein the time is for 3 minutes to 15 minutes.

24. The process of claim 18 wherein the sample comprises up to $10^6$ cultured cells.

25. The process of claim 18 wherein the surfactant comprises octylphenol ethoxylate having an average of 7.5 ethoxylate groups.

26. The process of claim 18 wherein the surfactant comprises octylphenol ethoxylate having an average of 9.5 ethoxylate groups.

27. The process of claim 18 wherein the surfactant comprises dodecyl alcohol polyoxyethylene ether having an average of 9.5 ethoxylate groups.

28. The process of claim 18 wherein the surfactant comprises octylphenolpoly(ethyleneglycolether).

* * * * *

```
                              SEQUENCE LISTING

<160> NUMBER OF SEQ ID NOS: 3

<210> SEQ ID NO 1
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: methoxysuccinyl derivative
<220> FEATURE:
<221> NAME/KEY: MOD_RES
<222> LOCATION: (4)..(4)
<223> OTHER INFORMATION: haloalkyl derivative, wherein halo is chloro,
      bromo, iodo, or fluoro and alkyl is C1-C3

<400> SEQUENCE: 1

Ala Ala Pro Val
1

<210> SEQ ID NO 2
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: methoxysuccinyl derivative
<220> FEATURE:
<221> NAME/KEY: MISC_FEATURE
<222> LOCATION: (3)..(3)
<223> OTHER INFORMATION: Pro or Leu
<220> FEATURE:
<221> NAME/KEY: MISC_FEATURE
<222> LOCATION: (4)..(4)
<223> OTHER INFORMATION: Ala or Val
<220> FEATURE:
<221> NAME/KEY: MOD_RES
<222> LOCATION: (4)..(4)
<223> OTHER INFORMATION: haloalkyl derivative, wherein halo is chloro,
      bromo, iodo, or fluoro and alkyl is C1-C3

<400> SEQUENCE: 2

Ala Ala Xaa Xaa
1

<210> SEQ ID NO 3
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: methoxysuccinyl derivative
<220> FEATURE:
<221> NAME/KEY: MOD_RES
<222> LOCATION: (4)..(4)
<223> OTHER INFORMATION: haloalkyl derivative, wherein halo is chloro,
      bromo, iodo, or fluoro and alkyl is C1-C

<400> SEQUENCE: 3

Ala Ala Pro Ala
1
```